(12) United States Patent
Conradie

(10) Patent No.: US 10,167,487 B2
(45) Date of Patent: Jan. 1, 2019

(54) METHODS, CELLS AND REAGENTS FOR PRODUCTION OF ISOPRENE, DERIVATIVES AND INTERMEDIATES THEREOF

(71) Applicant: INVISTA North America S.à.r.l., Wilmington, DE (US)

(72) Inventor: Alex Van Eck Conradie, Eaglescliffe (GB)

(73) Assignee: INVISTA North America S.à.r.l., Wilmington, DE (US)

( * ) Notice: Subject to any disclaimer, the term of this patent is extended or adjusted under 35 U.S.C. 154(b) by 18 days.

(21) Appl. No.: 15/238,234

(22) Filed: Aug. 16, 2016

(65) Prior Publication Data

US 2017/0051314 A1 Feb. 23, 2017

Related U.S. Application Data

(60) Provisional application No. 62/205,926, filed on Aug. 17, 2015.

(51) Int. Cl.
| | |
|---|---|
| *C12P 5/02* | (2006.01) |
| *C12P 19/32* | (2006.01) |
| *C12P 7/42* | (2006.01) |
| *C07C 11/18* | (2006.01) |
| *C08F 136/08* | (2006.01) |
| *C12P 5/00* | (2006.01) |
| *C12P 11/00* | (2006.01) |

(52) U.S. Cl.
CPC .............. *C12P 5/007* (2013.01); *C07C 11/18* (2013.01); *C08F 136/08* (2013.01); *C12P 7/42* (2013.01); *C12P 11/00* (2013.01); *C12P 19/32* (2013.01); *C12Y 102/07007* (2013.01); *C12Y 108/01004* (2013.01); *C12Y 401/01043* (2013.01); *C12Y 401/01074* (2013.01); *Y02E 50/343* (2013.01)

(58) Field of Classification Search
CPC .. C12P 5/007; C12P 7/42; C12P 11/00; C12Y 102/07007; C12Y 108/01004; C12Y 401/01043; C12Y 401/01074
USPC .................................................. 435/146, 167
See application file for complete search history.

(56) References Cited

U.S. PATENT DOCUMENTS

| | | |
|---|---|---|
| 2012/0045807 A1 | 2/2012 | Simpson et al. |
| 2013/0323820 A1 | 12/2013 | Chen et al. |

FOREIGN PATENT DOCUMENTS

| | | | | |
|---|---|---|---|---|
| WO | WO 2010/031062 A1 * | 3/2010 | ............... | C12P 5/02 |

OTHER PUBLICATIONS

Becker, et al., "Metabolic Flux Engineering of L-Lysine Production in Corynebacterium Glutamicum—Over Expression and Modification of G6P Dehydrogenase", Journal of Biotechnology, vol. 132, 2007, pp. 99-109.

(Continued)

*Primary Examiner* — Fred M Teskin
(74) *Attorney, Agent, or Firm* — Finnegan, Henderson, Farabow, Garrett & Dunner, LLP

(57) ABSTRACT

This application describes methods, including non-naturally occurring methods, for biosynthesizing 3-hydroxy-3-methylglutaryl-coA and intermediates thereof, as well as non-naturally occurring hosts for producing 3-hydroxy-3-methylglutaryl-coA. This application also describes methods, including non-naturally occurring methods, for biosynthesizing isoprene and intermediates thereof, as well as non-naturally occurring hosts for producing isoprene.

17 Claims, 8 Drawing Sheets

Specification includes a Sequence Listing.

(56) References Cited

OTHER PUBLICATIONS

Brigham, et al., "Engineering Ralstonia Eutropha for Production of Isobutanol from CO2, H2, and O2", Advanced Biofuels and Bioproducts, Springer New York, Chapter 39, 2013, pp. 1065-1090.
Bugg, et al., "The Emerging Role for Bacteria in Lignin Degradation and Bio-Product Formation", Current Opinion in Biotechnology, vol. 22, 2011, pp. 394-400.
Hermann, Thomas, "Industrial Production of Amino Acids by Coryneform Bacteria", Journal of Biotechnology, vol. 104, 2003, pp. 155-172.
Jaremko, et al., "The Initial Metabolic Conversion of Levulinic Acid in Cupriavidus Necator", Journal of Biotechnology, vol. 155, 2011, pp. 293-298.
Köpke, et al., "2, 3-Butanediol Production by Acetogenic Bacteria, An Alternative Route to Chemical Synthesis, Using Industrial Waste Gas", Applied and Environmental Microbiology, vol. 77, No. 15, 2011, pp. 5467-5475.
Kuzuyama, Tomohisa, "Mevalonate and Nonmevalonate Pathways for the Biosynthesis of Isoprene Units", Biosci. Biotechnol. Biochem., vol. 66, No. 8, 2002, pp. 1619-1627.
Lee, et al., "Synthesis of Pure Meso-2, 3-Butanediol from Crude Glycerol Using an Engineered Metabolic Pathway in *Escherichia coli*", Applied Biochemistry and Biotechnology, vol. 166, No. 7, 2012, pp. 1801-1813.
Li, et al., "Cupriavidus Necator JMP134 Rapidly Reduces Furfural With a Zn-Dependent Alcohol Dehydrogenase", Biodegradation, vol. 22, 2011, pp. 1215-1225.
Lim, et al., "Amplification of the NADPH-Related Genes zwf and gnd for the Oddball Biosynthesis of PHB in an *E. coli* Transformant Harboring a Cloned phbCAB Operon", Journal of bioscience and bioengineering, vol. 93, No. 6, 2002, pp. 543-549.
Martin, et al., "High-Titer Production of Monomeric Hydroxyvalerates from Levulinic Acid in Pseudomonas Putida", Journal of Biotechnology, vol. 139, No. 1, 2009, pp. 61-67.
Meijnen, et al., "Improved p-Hydroxybenzoate Production by Engineered Pseudomonas Putida S12 by Using A Mixed-Substrate Feeding Strategy", Applied Microbiology and Biotechnology, vol. 90, No. 3, 2011, pp. 885-893.
Ohashi, et al., "Continuous Production of Lactic Acid from Molasses by Perfusion Culture of Lactococcus Lactis Using a Stirred Ceramic Membrane Reactor", Journal of Bioscience and Bioengineering, vol. 87, No. 5, 1999, pp. 647-654.
Papanikolaou, et al., "Citric Acid Production by Yarrowia Lipolytica Cultivated on Olive-Mill Wastewater-Based Media", Bioresource Technology, vol. 99, 2008, pp. 2419-2428.
Perez-Pantoja, et al., "Metabolic Reconstruction of Aromatic Compounds Degradation from the Genome of the Amazing Pollutant-Degrading Bacterium Cupriavidus Necator JMP134", FEMS Microbiology Reviews, vol. 32, 2008, pp. 736-794.
Przybylski, et al., "Third-Generation Feed Stocks for the Clean and Sustainable Biotechnological Production of Bulk Chemicals: Synthesis of 2-Hydroxyisobutyric Acid", Energy, Sustainability and Society, vol. 2., No. 11, 2012, pp. 1-9.
Ramsay, et al., "Use of a Nylon Manufacturing Waste As an Industrial Fermentation Substrate", Applied and Environmental Microbiology, vol. 52, No. 1, 1986, pp. 152-156.
Seedorf, et al., "The Genome of Clostridium Kluyveri, a Strict Anaerobe with Unique Metabolic Features", Proceedings of the National Academy of Sciences, vol. 105, No. 6, 2008, pp. 2128-2133.
Wee, et al., "Biotechnological Production of Lactic Acid and its Recent Applications", Food Technology and Biotechnology, vol. 44, No. 2, 2006, pp. 163-172.
Whited, et al., "Technology Update: Development of a Gas-Phase Bioprocess for Isoprene-Monomer Production Using Metabolic Pathway Engineering", Peer Review, Industrial Biotechnology, vol. 6, No. 3, 2010, pp. 152-163.
Yang, et al., "Value-Added Uses for Crude Glycerol—A Byproduct of Biodiesel Production", Biotechnology for Biofuels, vol. 5, No. 13, 2012, pp. 1-10.

\* cited by examiner

FIG. 3A

| SEQ ID No. | GENBANK reference | Gene designation | Sequence Type | Sequence |
|---|---|---|---|---|
| 1 | BAB58707.1 | mvaA | Amino Acid | MQSLDKNFRHLSRQQKLQQLVDKQWLSEDQFDILLNHPLIDEEVANSLIENVIAQGAL PVGLLPNIIVDDKAYVVPMMVEEPSVVAAASYGAKLVNQTGGFKTVSSERIMIGQIVF DGVDDTEKLSADIKALEKQIHKIADEAYPSIKARGGGYQRIAIDTFPEQQLLSLKVFVD TKDAMGANMLNTILEAITAFLKNESPQSDILMSILSNHATASVVKVQGEIDVKDLARGE RTGEEVAKRMERASVLAQVDIHRAATHNKGVMNGIHAVVLATGNDTRGAEASAHAY ASRDGQYRGIATWRYDQKRQRLIGTIEVPMTLAIVGGGTKVLPIAKASLELLNVDSAQ ELGHVVAAVGLAQNFAACRALVSEGIQQGHMSLQYKSLAIVVGAKGDEIAQVAEALK QEPRANTQVAERILQEIRQQ |
| 2 | BAB56752.1 | mvaK1 | Amino Acid | MAVPFNAGKIKVLIEALESGNYSSIKSDVVYDGMLYDAPDHLKSLVNRFVELNNITEPL AVTIQTNLPPSRGLGSSAAVAVAFVRASYDFLGKSLTKEELIEKANWAEQIAHGKPSG IDTQTIVSGKPVWFQKGHAETLKTLSLDGYMVVIDTGVKGSTRQAVEDVHKLCEDPQ YMSHVKHIGKLVLRASDVIEHHNFEALADIFNECHADLKALTVSHDKIEQLMKIGKEN GAIAGKLTGAGRGGSMLLLAKDLPTAKNIVKAVEKAGAAHTWIENLGG |
| 3 | BAB56754.1 | mvaK2 | Amino Acid | MIQVKAPGKLYIAGEYAVTEPGYKSVLIALDRFVTATIEEADQYKGTIHSKALHHNPVT FSRDEDSIVISDPHAAKQLNYVVTAIEIFEQYAKSCDIAMKHFHLTIDSNLDDSNGHKY GLGSSAAVLVSVIKVLNEFYDMKLSNLYIYKLAVIANMKLQSLSSCGDIAVSVYSGWL AYSTFDHEWVKHQIEDTTVEEVLIKNWPGLHIEPLQAPENMEVLIGWTGSPASSPHF VSEVKRLKSDPSFYGDFLEDSHRCVEKLIHAFKTNNIKGVQKMVRQNRTIIQRMDKE ATVDIETEKLKYLCDIAEKYHGASKTSGAGGDCGITIINKDVDKEKIYDEWTKHGIKP LKFNIYHGQ |
| 4 | AAK99143.1 | Mdd | Amino Acid | MYHSLGNQFDTRTRTSRKIRRERSCSDMDREPVTVRSYANIAIIKYWGKKEKEMVP ATSSISLTLENMYTETTLSPLPANVTADEFYINGQLQNEVEHAKMSKIIDRYRPAGEG FVRIDTQNNMPTAAGLSSSSSGLSALVKACNAYFKLGLDRSQLAQEAKFASGSSSR SFYGPLGAWDKDSGEIYPVETDLKLAMIMLVLEDKKPISSRDGMKLCVETSTTFDD WVRQSEKDYQDMLIYLKENDFAKIGELTEKNALAMHATTKTASPAFSYLTDASYEAM DFVRQLREKGEACYFTMDAGPNVKVFCQEKDLEHLSEIFGQRYRLIVSKTKDLSQDD CC |
| 5 | AAG02436.1 | Mdd | Amino Acid | MVKSGKARAHTNIALIKYWGKADETYIIPMNNSLSVTLDRFYTETKVTFDPDFTEDCLI LNGNEVNAKEKEKIQNYMNIVRDLAGNRLHARIESENYVPTAAGLASSASAYAALAA ACNEALSLNLSDTDLSRLARRGSGSASRSIFGGFAEWEKGHDDLTSYAHGINSNGW EKDLSMIFVVINNQSKKVSSRSGMSLTRDTSRFYQYWLDHVDEDLNEAKEAVKNQD FQRLGEVIEANGLRMHATNLGAQPPFTYLVQESYDAMAIVEQCRKANLPCYFTMDA GPNVKVLVEKKNKQAVMEQFLKVFDESKIIASDIISSGVEIIK |

FIG. 3B

| SEQ ID No. | GENBANK reference | Gene designation | Sequence Type | Sequence |
|---|---|---|---|---|
| 6 | ABX19602.1 | idi | Amino Acid | MEERLILVDTDDRPIGICEKMRAHHEGLLHRAFSIFVFDSAGRLLLQQRALNKYHSGG LWSNTCCGHPRPREALPDAVRRLGEEMGFACELRPVDALVYRARFENDLIEHEFV HIHVGRFDGTVAPDFAEVAAWRWIDVPTLLEWMADEPSAFTVWFHCMIERAGLPVL HRWAHR |
| 7 | | ispS | Amino Acid | MATNPSCLSTPFLSSTPALSTRFPLSENFTQKTSLVNPKPWPLISAVSSQFSQIAEDN SRRSANYHPNLWDFEFLQSLENDSKMEKLEEKATKLEEEVRNMMNEAKTEALSLLE LIDDVQRLGLTYKFEKDIIKALEKIVPLDESGLHVTSLSFRILRQHGFEVSQDVFKRFK DKEGGFCAELKDDVQGLLSLYEASYLGFEGESLLDEARAFSITHLKNNLNKGINTKVA QQVSHALELPYHRRLHRLEARWLLDKYEPKEPHHHLLHELAKLDFNLVQSLYQKELR ELSLWWREIGLTSKLDFVRDRLMEVYFWALGMAPDPQFSECRKVVTKMFGLVTIIDD VYDVYGTLDELQLFTDAVERWDVNAINTLPDYMKLCYLALYNTVNDTAYSILKEKGH NNISYLTKSWCELCKAFLQEAKWSNNKIIPAFNKYLDNASVSSSGVALLAPSYFLVCQ EQDISDQALHSLTNFHGLVRSSCTIFRLCNDLATSSAELERGETTNSITSYMHENETS EEQACKELRNLIDAEWKKMNEERVSNSTLPKAFREIAINMARISHCTYQYGDGLGRP DYTTENRIKLLLIDPFPIN |

FIG. 4A

| SEQ ID No. | Gene designation | Sequence Type | Sequence |
|---|---|---|---|
| 8 | mvaA | Nucleotide | CTATTGTTGTCTAATTTCTTGTAAAATGCGTTCAGCTACTTGTGTATTCGCACGGGGTTCTTG CTTCAATGCTTCAGCTACTTGCGCATTTCATCACCTTTGCACCTACAACAATAGCTAAAGA TTTATATTGCAAGCTCATATGGCCTTGCTGGATACCTTCGGAAACGAGCGCGACATGCTG CAAAGTTCTGTGCTAAACCAACGGCAGCAACTACATGACCTAATTCTTGTGCTGAATCTACA TTAGCAATTCTAAAGAAGCTTAGCAATTGGTAATACTTTGTACCACCGCCAACGATTGCC AATGTCATAGGCACTTCTATTGTACCAATTAAACGTTGACGTTTTGATCGTATCTCCATGTT GCAATACCACGATACTGTCCGTCACGACTGCTATGCATGCGCACTTGCTTCTGCACCAC GCGTATCATTCCTGTTGCTAAAACAACGGCATGTATGCCATTCATAACACCTTTATTATGTG TTGCAGCACGATGAATATCAACTTGTGCCAAATACAGAAGACACGTTCCATTCGTTTGGCAACC TCTTCTCCAGTTCTCTCGCCCCCCTTGCTAAAATCTTTAACGTCAATTTGCCTTGTGGAGATTCATTT ACGGACGCGTGTTGCAGTTATGGCCTCTAAAATACTCATTAAAATGTCGCTTTGTGGAGATTCATT TTTAAAAATGCAGTTATGGCCTCTAAAATAGTAACTGTTGCTCAGGAAATGTATCAATAGCTATACGT GTATCAACAAATACTTTAAAGATAGTAACTGTTGCTCAGGAAATGTATCAATAGCTATACGT TGGTAACCACCACGCGCTTAATGAGAAGGATATGCCTCATCGTCAAGCCATCAAAGACGAT CTTTTCTAAAGCTTAATGTCTGCTGATAATTTTCAGTATCGTCAAGCCATCGATTCACTAGCTT TGACCTATCATAATACGTTCAGAGCGACAACTCGGTAATAATCCAACGGGTAATGCACCTTGCGGATGACA CCTTATCGTCCACAATGATATTCGGTAATAATCCAACGGGTAATGCACCTTGCGGATGACA TTTTCAATTAAAACTATTTGCTACTTCCTCATCAATTAATGGATGATTCAATAAATGTCGAATT GATCTTCTGATAAACCATTGCTTATCTACCCAATTGTTGTAACTTTTGTTGACGAGATAAATGTC GGAAATTCTTATCTAAACTTTGCAT |
| 9 | mvaK1 | Nucleotide | ATTGCAGTACCGTTTAACGCAGGTAAAATCAAAGTTTTAATAGAAGCCTTAGAGAGCGGGAA CTATTCGTCTATTAAAAAGCGATGTTTACGATGGTATGTTATATGATGCGCCTGACCATCTAA GTCTTTGGTGAACCGTTTGTAGAATTAAATAATATTACAGAGCCGCTAGCAGTAACGATCCA AACGAATTTACCACCATCACGTGGATTAGGATCGAGTCGCAGCTGTCGCGGTTGCTTTGTC GTGCAAGTTATGATTTTTAGGGAAATCATTAACGAAAGAAGAACTCATTGAAAAGGCTAATT GGGCAGAGCAAATTGCCAAAAGGTCAACCAAGTGTATTGATACGCAACATTAAGTTTAGACGGCT CAAACCAGTTGTTGTTATTGAGGATCCTCAGTAGCTCATGCTGAAAGGTTCATGCATGTCAACATGTCACATGTGT ATATGGTTGTTATTGAGGATCCTCAGTAGCTCATGTGAACATCTAAACTTTGAAGCCCTAGCGGGATATTTTTAATCGT AAACTTTGTGAGGATCCTCAGTAGCTCATGTGAACATCTAAACATATCGGTAAGTTAGTTTACGT GCGAGTGATGTGAAAGGCGTTGAAGACATCATAACTTAGTCATGATAAGAACAATTAATGAAAATTGGTAAA GCGGATTTAACAACAGCGAAAAATATTGTGAAAGCTGTAGAAAGCTGTGGTGCAGCAC ATACATGGATTGAGAATTTAGGAGGTTAA |

FIG. 4B

| SEQ ID No. | Gene designation | Sequence Type | Sequence |
|---|---|---|---|
| 10 | mvaK2 | Nucleotide | ATGATTCAGGTCAAAGCACCCGGAAAACTTTATATTGCTGGAGAATATGCTGTAACAGAACC<br>AGGATATAAATCTGTACTTATTGCGTTAGATCGTTTTGTAACTGCTACTATTGAAGAAGCAGA<br>CCAATATAAAGGTACCATTCATTCAAAAGCATTACATCATAACCCAGTTACATTTAGTAGAGA<br>TGAAGATAGTATTGTCATTTCAGATCCACATGCAGAAAACATTAAATTATGTGGTCACAGC<br>TATTGAAATATTTGACAATAGCCGAAAAGTTGCGATATAGCGATGAAGCATTTTCATCTGAC<br>TATTGATAGTAATTTAGATGATTCAAATGGTCATAAATATGATTAGGTTCAAGTGCAGCAGT<br>ACTTGTGTCAGTTATAAAGTATTAAATGAAGTTACAAAGTTTCATGCGGAGATATTGCTG<br>ATAAACTAGCAGTGATTGGAGTGTATATAGTGGTTAGCGTATAGTACTTTAAGTTCATGAA<br>TGAGTGTATATACTACGGTTGAAGAAGTTTAATCAAAAACTGGCCTGGATTGCACATCGAACCA<br>TTACAAGCACCTGAAAATATGGAAGTACTTATCGGTTGGACTGATCCTCATTTAAAACAAATAACATTAAAGGTGT<br>ACACTTTGTAGCGAAGTCGTTGTTGAAACGTTTGAAATCAGATCCTCATTTAAAACAAATAACATTAAAGGTGT<br>AGATTCACATCGTTGTGCGTCAGATAGCTAAAATCGTACAATTATTCAACGTATGGATAAAAGAAGCTACAGTTG<br>GCAAAAGATGGTGCGTCAGATAGCTAAAATATTTGTGTGATATTGCTGAAAAGTATCACGGTGCATCTA<br>ATATAGAAACTGAAAAGCTAAAATATTTGTGTGATATTGCTGAAAAGTATCACGGTGCATCTA<br>AACATCAGGCGCTGGTGGTGACAATGGACAAACATGTATTAAACCATTAAAATTTAATATTTATCATG<br>GAAAAAATTTATGATGAATGGACAAACATGTATTAAACCATTAAAATTTAATATTTATCATG<br>GGCAATAA |
| 11 | mdd | Nucleotide | TTGTATCATAGCCTTGGTAACCAATTTGACACACGCACAAGAACTAGCAGAAAGATTAGAAG<br>AGAAAGGAGCTGTTCAGACAGCTGTGACAGTACGTTCCTACGCAAATATT<br>GCTATTATCAAATATTGGGGAAAGAGAAAAAGAGATGGTGCCTGCTACTAGCAGTAT<br>TTCTCTAACTTTGGAAATTTACATCAATGGTCAGCTACAAAATGAGGTCGAGCATGCCAAGATGAGTA<br>AGCTGACGAATTATTGACCGTTATCGTCCAGCTGGTCAGCTACAAAATGAGGTCGAGCATGCCAAGATGAGTA<br>AGATTATTGACCGTTATCGTCCAGCTGGTGCAAGTTCTAGTGAAGTCAGTTAGGCCTCTGCCGCCCTGGTCAAGGCTT<br>ATGCCTACGGCAGCGGGCCTGTCCTCAAGTTGCAAGTGCCGATGCCTCGGCCCCTGGTCAAGGCTT<br>GTAATGCTTATTTCAAGCTTGGATTGGATAGAAGTCAGTTAGCGCAGGAAGCCAAGTTTGCC<br>TCAGGCTCTCTTCTCGTAGAGACAGACTTGAAACTGCTACCGGAGCCTGGGATAAGGATAGTGGAG<br>AAATTTACCCTGTCAGTCTGAGAAGACAGACTTGAAACTGATTATCTCAAGGAAATG<br>AAAAACCAATCTCTAGCCGTGACGGGATGAAACTTTGTGTGAAACCTCGACGACTTTCGA<br>CGACTGGGTTCGTCAGTCTGAGAAGGACGACTATCAGGATATGCTGATTTATCTCAAGGAAATG<br>ATTTTGCCAAGATTCCAGCCTTTTCTTACCTGTAGAAGGAGGGCCTGCTACTTTACCATGGATGCCTATGCATGCTACGACAAAG<br>ACTGCAGTCCAGCCTTTTCTTATCTGACGGAGCCTGCTACTTTACCATGGATGCCTATGCATGCTACGACAAAG<br>TCAGCTTCGTGCAGATTGGAAAGGAGAGACTTGGAGCATTTGTGCAGAAATTTTCGGTCGTGGTTATCGCTT<br>GTCTTCTGTCAGGAGAAAACAAAGGATTTGAGTCAAGATGATTGCTGTTAA<br>GATTGTGTCAAAAACAAAGGATTTGAGTCAAGATGATTGCTGTTAA |

FIG. 4C

| SEQ ID No. | Gene designation | Sequence Type | Sequence |
|---|---|---|---|
| 12 | idi | Nucleotide | TCATCTGTGTGCCCAGCGATGCAGCACTGGCAATCCGGCTCGCTCTATCATGCAGTGGAAC CAGACAGTAAAAGCGCTCGGCTCGTCCCGCCATCCACTCCAGCAAGGTTGGCACATCGATCC ATCGCCACGCGCTACTTCCGCGAAATCTGGGGCGACCGTTCCATCGAACGACCAACATG AATATGCACAAACTCGTGCTCGATCAGGTCGTTCTCAAATCTCGCGCGGTACACGAGCGCG TCCACGGGCCGAAGTTCACATGCGAATCCCATTTCTTCGCCAAGCCGGGCGCAACCGCAT CAGGCAGCGCTTCGCGTGGACGCGGTGCCCGCAGCATGTGTTGGACCACAGCCCGCCC GAGTGGTACTTATTCAGCGCACGCTGCTGTAGCAGCAAGCGACCGGCGAGTCGAACACA AAAATCGAGAATGCGCGGTGCAGCAGCCCTTCATGGTGCGCGCATCTTCTCGCATATTC CTATCGGTCGATCGTCGGTATCGACGAGGATCAGGCGTTCTTCCAT |

FIG. 4D

| SEQ ID No. | Gene designation | Sequence Type | Sequence |
|---|---|---|---|
| 13 | ispS | Nucleotide | ATGGCAACCAACCCTTCATGTCTTATCTACTCCATTTTGTCTCCACACCAGCACTAAGTACT AGATTTCCATTAAGTGAGAACTTCACACAAAAACATCTCTTGTCAATCCCAAACCTTGGCCA CTTATTTCTGCAGTCAGCTCTCAATTTAGCCAAATAGCAGAAGATAATAGTCGTCGTTCAGCT AATTACCACCCAAACCTCTGGGATTTTGAATTTCTGCAGTCTCTCGAAATGACTCTAAGATG GAAAAGCTGGAAGAGAGAAAGCAACAAAGTTGGAGGAGAAGTGCGAAACATGATGAACGAAG CAAAGACAGAAGCACTAAGCTTATTGGAATTGATAGACGACGTCCAGCGTCTGGGATTGAC CTACAAGTTTGAGAAGGACATAATCAAAGCCCTTGAGAAGATTGTTCCATTGGATGAGAGTG GGCTGCATGTTACTTCTCTCCAGCTTCCGTATACTTAGACAACATGGCTTTGAGGTTTCCCAA GATGTGTTTAAGAGATTTAAGGACAAGGAGGAGCATCCTATCTTGGTTTGTGCTGAACTTAAAGACGATGT TCAAGGGTTGCTAAGTCTATATGAAGCATCTCAAGAACAACCTAAACAAGGAATAAACACC ACGAGGCAAGGCATTTCAATAACACATCTCAAGAACAACCTAAACAAGGAATAAACACC AAAGTAGCCCAACAAGTTAGCCATGCACTGGAACTTCCTATCATCGAAGACTGCATAGACT GGAAGCACGACGTGGCTCCTTGACAAATATGAACCAAAGGAACCCCACCATCATTTACTACACG AGCTTGCAAGTTGGATTTCAATTTGGTCCAATCATTGTACCAGAAAGAGTTGCGAGAATTG TCACTGTGGTGGAGGGAGATTGGGCTCACAAGCAAGTTGGACTTTGTTCGAGACAGATTAA TGGAAGTGTACTTTTGGGCGCTGGGAATGGCACCTGATCCTCAATTTAGTGAATGTCGTAAA GTCGTCACTAAAATGTTGGGCTAGTACTTACTATCATCGATGATGTATATGACGTTTACGGTACT TTGGACGAGCTACAACTCTTCACCGATGCTGTTAGCCCTTTATAACACCGTCAATGACACAGCTT CACTTCCAGACTATATGAAATTGTGCTATTTGACAAATCTGGTGTGAGT ATAGCATCCTTAAAGAAAAGGGACATAACAGCAAATGGTCAAACAACAAATCATTCCAGCATTCAAC TGTGCAAAGCATTCCTCCAAGAAGCATGCGGTGTCCTCCTGGTGTGGCTTGCTTGCTCCTTCCTACTT AAGTACCTAGACAATGCATCGGTGTCTCCTGGTGTGGCTTGCTTGCTCCTTCCTACTT CTTAGTGTGCCAAGAACAAGACATTTCAGACCAAGCTCTTCATTCCTTAACTAATTTCCATGG CCCTTGTGCGTTCATCATGCACCATTTTTAGGCTTTGCAATGATCTGGCTACCTCATCGGCTG AGCTAGAGAGAAGGTGAAACAACAAATTCAATCACATCGTACATGCATGAGAATGAGACTTCT GAGGAGCAAGCATGTAAGGAGTTGAGAAATTTGATCGATGCAGAGTGGAAGAAGATGAATG AAGAGCGAGTTTCAAATTCTACACTCCAAAAGCATTTAGGGAAATAGCTATTAACATGGCT CGGATTTCCCATTGCACATACCAATATGGAGACGGACTTGGAAGGCCGACTACACCACAG AGAACAGGATAAAGTTGCTACTAATAGACCCTTTCCAATTAATTAG |

SEQUENCE LISTING

<160> NUMBER OF SEQ ID NOS: 14

<210> SEQ ID NO 1
<211> LENGTH: 425
<212> TYPE: PRT
<213> ORGANISM: Staphylococcus aureus

<400> SEQUENCE: 1

| Met | Gln | Ser | Leu | Asp | Lys | Asn | Phe | Arg | His | Leu | Ser | Arg | Gln | Gln | Lys |
|---|---|---|---|---|---|---|---|---|---|---|---|---|---|---|---|
| 1 | | | | 5 | | | | | 10 | | | | | 15 | |

| Leu | Gln | Gln | Leu | Val | Asp | Lys | Gln | Trp | Leu | Ser | Glu | Asp | Gln | Phe | Asp |
|---|---|---|---|---|---|---|---|---|---|---|---|---|---|---|---|
| | | | 20 | | | | | 25 | | | | | 30 | | |

| Ile | Leu | Leu | Asn | His | Pro | Leu | Ile | Asp | Glu | Glu | Val | Ala | Asn | Ser | Leu |
|---|---|---|---|---|---|---|---|---|---|---|---|---|---|---|---|
| | | 35 | | | | | 40 | | | | | 45 | | | |

| Ile | Glu | Asn | Val | Ile | Ala | Gln | Gly | Ala | Leu | Pro | Val | Gly | Leu | Leu | Pro |
|---|---|---|---|---|---|---|---|---|---|---|---|---|---|---|---|
| | 50 | | | | | 55 | | | | | 60 | | | | |

| Asn | Ile | Ile | Val | Asp | Asp | Lys | Ala | Tyr | Val | Pro | Met | Met | Val | Glu |
|---|---|---|---|---|---|---|---|---|---|---|---|---|---|---|
| 65 | | | | | 70 | | | | 75 | | | | | 80 |

| Glu | Pro | Ser | Val | Val | Ala | Ala | Ala | Ser | Tyr | Gly | Ala | Lys | Leu | Val | Asn |
|---|---|---|---|---|---|---|---|---|---|---|---|---|---|---|---|
| | | | | 85 | | | | | 90 | | | | | 95 | |

| Gln | Thr | Gly | Gly | Phe | Lys | Thr | Val | Ser | Ser | Glu | Arg | Ile | Met | Ile | Gly |
|---|---|---|---|---|---|---|---|---|---|---|---|---|---|---|---|
| | | | 100 | | | | | 105 | | | | | 110 | | |

| Gln | Ile | Val | Phe | Asp | Gly | Val | Asp | Asp | Thr | Glu | Lys | Leu | Ser | Ala | Asp |
|---|---|---|---|---|---|---|---|---|---|---|---|---|---|---|---|
| | | | 115 | | | | | 120 | | | | | 125 | | |

| Ile | Lys | Ala | Leu | Glu | Lys | Gln | Ile | His | Lys | Ile | Ala | Asp | Glu | Ala | Tyr |
|---|---|---|---|---|---|---|---|---|---|---|---|---|---|---|---|
| | | 130 | | | | | 135 | | | | | 140 | | | |

| Pro | Ser | Ile | Lys | Ala | Arg | Gly | Gly | Tyr | Gln | Arg | Ile | Ala | Ile | Asp |
|---|---|---|---|---|---|---|---|---|---|---|---|---|---|---|
| 145 | | | | | 150 | | | | 155 | | | | | 160 |

| Thr | Phe | Pro | Glu | Gln | Gln | Leu | Leu | Ser | Leu | Lys | Val | Phe | Val | Asp | Thr |
|---|---|---|---|---|---|---|---|---|---|---|---|---|---|---|---|
| | | | | 165 | | | | | 170 | | | | | 175 | |

| Lys | Asp | Ala | Met | Gly | Ala | Asn | Met | Leu | Asn | Thr | Ile | Leu | Glu | Ala | Ile |
|---|---|---|---|---|---|---|---|---|---|---|---|---|---|---|---|
| | | | 180 | | | | | 185 | | | | | 190 | | |

| Thr | Ala | Phe | Leu | Lys | Asn | Glu | Ser | Pro | Gln | Ser | Asp | Ile | Leu | Met | Ser |
|---|---|---|---|---|---|---|---|---|---|---|---|---|---|---|---|
| | | 195 | | | | | 200 | | | | | 205 | | | |

| Ile | Leu | Ser | Asn | His | Ala | Thr | Ala | Ser | Val | Val | Lys | Val | Gln | Gly | Glu |
|---|---|---|---|---|---|---|---|---|---|---|---|---|---|---|---|
| | 210 | | | | | 215 | | | | | 220 | | | | |

| Ile | Asp | Val | Lys | Asp | Leu | Ala | Arg | Gly | Glu | Arg | Thr | Gly | Glu | Glu | Val |
|---|---|---|---|---|---|---|---|---|---|---|---|---|---|---|---|
| 225 | | | | | 230 | | | | 235 | | | | | 240 |

| Ala | Lys | Arg | Met | Glu | Arg | Ala | Ser | Val | Leu | Ala | Gln | Val | Asp | Ile | His |
|---|---|---|---|---|---|---|---|---|---|---|---|---|---|---|---|
| | | | | 245 | | | | | 250 | | | | | 255 | |

| Arg | Ala | Ala | Thr | His | Asn | Lys | Gly | Val | Met | Asn | Gly | Ile | His | Ala | Val |
|---|---|---|---|---|---|---|---|---|---|---|---|---|---|---|---|
| | | | 260 | | | | | 265 | | | | | 270 | | |

| Val | Leu | Ala | Thr | Gly | Asn | Asp | Thr | Arg | Gly | Ala | Glu | Ala | Ser | Ala | His |
|---|---|---|---|---|---|---|---|---|---|---|---|---|---|---|---|
| | | 275 | | | | | 280 | | | | | 285 | | | |

| Ala | Tyr | Ala | Ser | Arg | Asp | Gly | Gln | Tyr | Arg | Gly | Ile | Ala | Thr | Trp | Arg |
|---|---|---|---|---|---|---|---|---|---|---|---|---|---|---|---|
| | 290 | | | | | 295 | | | | | 300 | | | | |

| Tyr | Asp | Gln | Lys | Arg | Gln | Arg | Leu | Ile | Gly | Thr | Ile | Glu | Val | Pro | Met |
|---|---|---|---|---|---|---|---|---|---|---|---|---|---|---|---|
| 305 | | | | | 310 | | | | 315 | | | | | 320 |

| Thr | Leu | Ala | Ile | Val | Gly | Gly | Gly | Thr | Lys | Val | Leu | Pro | Ile | Ala | Lys |
|---|---|---|---|---|---|---|---|---|---|---|---|---|---|---|---|
| | | | | 325 | | | | | 330 | | | | | 335 | |

| Ala | Ser | Leu | Glu | Leu | Leu | Asn | Val | Asp | Ser | Ala | Gln | Glu | Leu | Gly | His |
|---|---|---|---|---|---|---|---|---|---|---|---|---|---|---|---|
| | | | 340 | | | | | 345 | | | | | 350 | | |

| Val | Val | Ala | Ala | Val | Gly | Leu | Ala | Gln | Asn | Phe | Ala | Ala | Cys | Arg | Ala |
|---|---|---|---|---|---|---|---|---|---|---|---|---|---|---|---|
| | | 355 | | | | | 360 | | | | | 365 | | | |

```
Leu Val Ser Glu Gly Ile Gln Gln Gly His Met Ser Leu Gln Tyr Lys
        370                 375                 380

Ser Leu Ala Ile Val Val Gly Ala Lys Gly Asp Glu Ile Ala Gln Val
385                 390                 395                 400

Ala Glu Ala Leu Lys Gln Glu Pro Arg Ala Asn Thr Gln Val Ala Glu
                405                 410                 415

Arg Ile Leu Gln Glu Ile Arg Gln Gln
                420                 425

<210> SEQ ID NO 2
<211> LENGTH: 279
<212> TYPE: PRT
<213> ORGANISM: Staphylococcus aureus

<400> SEQUENCE: 2

Met Ala Val Pro Phe Asn Ala Gly Lys Ile Lys Val Leu Ile Glu Ala
1               5                   10                  15

Leu Glu Ser Gly Asn Tyr Ser Ser Ile Lys Ser Asp Val Tyr Asp Gly
                20                  25                  30

Met Leu Tyr Asp Ala Pro Asp His Leu Lys Ser Leu Val Asn Arg Phe
            35                  40                  45

Val Glu Leu Asn Asn Ile Thr Glu Pro Leu Ala Val Thr Ile Gln Thr
        50                  55                  60

Asn Leu Pro Pro Ser Arg Gly Leu Gly Ser Ser Ala Ala Val Ala Val
65                  70                  75                  80

Ala Phe Val Arg Ala Ser Tyr Asp Phe Leu Gly Lys Ser Leu Thr Lys
                85                  90                  95

Glu Glu Leu Ile Glu Lys Ala Asn Trp Ala Glu Gln Ile Ala His Gly
                100                 105                 110

Lys Pro Ser Gly Ile Asp Thr Gln Thr Ile Val Ser Gly Lys Pro Val
            115                 120                 125

Trp Phe Gln Lys Gly His Ala Glu Thr Leu Lys Thr Leu Ser Leu Asp
        130                 135                 140

Gly Tyr Met Val Val Ile Asp Thr Gly Val Lys Gly Ser Thr Arg Gln
145                 150                 155                 160

Ala Val Glu Asp Val His Lys Leu Cys Glu Asp Pro Gln Tyr Met Ser
                165                 170                 175

His Val Lys His Ile Gly Lys Leu Val Leu Arg Ala Ser Asp Val Ile
            180                 185                 190

Glu His His Asn Phe Glu Ala Leu Ala Asp Ile Phe Asn Glu Cys His
        195                 200                 205

Ala Asp Leu Lys Ala Leu Thr Val Ser His Asp Lys Ile Glu Gln Leu
210                 215                 220

Met Lys Ile Gly Lys Glu Asn Gly Ala Ile Gly Lys Leu Thr Gly
225                 230                 235                 240

Ala Gly Arg Gly Gly Ser Met Leu Leu Leu Ala Lys Asp Leu Pro Thr
                245                 250                 255

Ala Lys Asn Ile Val Lys Ala Val Glu Lys Ala Gly Ala Ala His Thr
            260                 265                 270

Trp Ile Glu Asn Leu Gly Gly
        275

<210> SEQ ID NO 3
<211> LENGTH: 358
<212> TYPE: PRT
<213> ORGANISM: Staphylococcus aureus
```

<400> SEQUENCE: 3

```
Met Ile Gln Val Lys Ala Pro Gly Lys Leu Tyr Ile Ala Gly Glu Tyr
  1               5                  10                  15

Ala Val Thr Glu Pro Gly Tyr Lys Ser Val Leu Ile Ala Leu Asp Arg
             20                  25                  30

Phe Val Thr Ala Thr Ile Glu Glu Ala Asp Gln Tyr Lys Gly Thr Ile
         35                  40                  45

His Ser Lys Ala Leu His His Asn Pro Val Thr Phe Ser Arg Asp Glu
 50                  55                  60

Asp Ser Ile Val Ile Ser Asp Pro His Ala Ala Lys Gln Leu Asn Tyr
 65                  70                  75                  80

Val Val Thr Ala Ile Glu Ile Phe Glu Gln Tyr Ala Lys Ser Cys Asp
             85                  90                  95

Ile Ala Met Lys His Phe His Leu Thr Ile Asp Ser Asn Leu Asp Asp
             100                 105                 110

Ser Asn Gly His Lys Tyr Gly Leu Gly Ser Ser Ala Ala Val Leu Val
             115                 120                 125

Ser Val Ile Lys Val Leu Asn Glu Phe Tyr Asp Met Lys Leu Ser Asn
 130                 135                 140

Leu Tyr Ile Tyr Lys Leu Ala Val Ile Ala Asn Met Lys Leu Gln Ser
145                 150                 155                 160

Leu Ser Ser Cys Gly Asp Ile Ala Val Ser Val Tyr Ser Gly Trp Leu
             165                 170                 175

Ala Tyr Ser Thr Phe Asp His Glu Trp Val Lys His Gln Ile Glu Asp
             180                 185                 190

Thr Thr Val Glu Glu Val Leu Ile Lys Asn Trp Pro Gly Leu His Ile
             195                 200                 205

Glu Pro Leu Gln Ala Pro Glu Asn Met Glu Val Leu Ile Gly Trp Thr
 210                 215                 220

Gly Ser Pro Ala Ser Ser Pro His Phe Val Ser Glu Val Lys Arg Leu
225                 230                 235                 240

Lys Ser Asp Pro Ser Phe Tyr Gly Asp Phe Leu Glu Asp Ser His Arg
             245                 250                 255

Cys Val Glu Lys Leu Ile His Ala Phe Lys Thr Asn Asn Ile Lys Gly
             260                 265                 270

Val Gln Lys Met Val Arg Gln Asn Arg Thr Ile Ile Gln Arg Met Asp
             275                 280                 285

Lys Glu Ala Thr Val Asp Ile Glu Thr Glu Lys Leu Lys Tyr Leu Cys
 290                 295                 300

Asp Ile Ala Glu Lys Tyr His Gly Ala Ser Lys Thr Ser Gly Ala Gly
305                 310                 315                 320

Gly Gly Asp Cys Gly Ile Thr Ile Asn Lys Asp Val Asp Lys Glu
             325                 330                 335

Lys Ile Tyr Asp Glu Trp Thr Lys His Gly Ile Lys Pro Leu Lys Phe
             340                 345                 350

Asn Ile Tyr His Gly Gln
             355
```

<210> SEQ ID NO 4
<211> LENGTH: 344
<212> TYPE: PRT
<213> ORGANISM: Streptococcus pneumoniae

<400> SEQUENCE: 4

Met Tyr His Ser Leu Gly Asn Gln Phe Asp Thr Arg Thr Arg Thr Ser
1               5                   10                  15

Arg Lys Ile Arg Arg Glu Arg Ser Cys Ser Asp Met Asp Arg Glu Pro
                20                  25                  30

Val Thr Val Arg Ser Tyr Ala Asn Ile Ala Ile Ile Lys Tyr Trp Gly
            35                  40                  45

Lys Lys Lys Glu Lys Glu Met Val Pro Ala Thr Ser Ser Ile Ser Leu
50                  55                  60

Thr Leu Glu Asn Met Tyr Thr Glu Thr Thr Leu Ser Pro Leu Pro Ala
65                  70                  75                  80

Asn Val Thr Ala Asp Glu Phe Tyr Ile Asn Gly Gln Leu Gln Asn Glu
                85                  90                  95

Val Glu His Ala Lys Met Ser Lys Ile Ile Asp Arg Tyr Arg Pro Ala
            100                 105                 110

Gly Glu Gly Phe Val Arg Ile Asp Thr Gln Asn Asn Met Pro Thr Ala
        115                 120                 125

Ala Gly Leu Ser Ser Ser Ser Gly Leu Ser Ala Leu Val Lys Ala
130                 135                 140

Cys Asn Ala Tyr Phe Lys Leu Gly Leu Asp Arg Ser Gln Leu Ala Gln
145                 150                 155                 160

Glu Ala Lys Phe Ala Ser Gly Ser Ser Arg Ser Phe Tyr Gly Pro
                165                 170                 175

Leu Gly Ala Trp Asp Lys Asp Ser Gly Glu Ile Tyr Pro Val Glu Thr
            180                 185                 190

Asp Leu Lys Leu Ala Met Ile Met Leu Val Leu Glu Asp Lys Lys Lys
        195                 200                 205

Pro Ile Ser Ser Arg Asp Gly Met Lys Leu Cys Val Glu Thr Ser Thr
210                 215                 220

Thr Phe Asp Asp Trp Val Arg Gln Ser Glu Lys Asp Tyr Gln Asp Met
225                 230                 235                 240

Leu Ile Tyr Leu Lys Glu Asn Asp Phe Ala Lys Ile Gly Glu Leu Thr
                245                 250                 255

Glu Lys Asn Ala Leu Ala Met His Ala Thr Thr Lys Thr Ala Ser Pro
            260                 265                 270

Ala Phe Ser Tyr Leu Thr Asp Ala Ser Tyr Glu Ala Met Asp Phe Val
        275                 280                 285

Arg Gln Leu Arg Glu Lys Gly Glu Ala Cys Tyr Phe Thr Met Asp Ala
290                 295                 300

Gly Pro Asn Val Lys Val Phe Cys Gln Glu Lys Asp Leu Glu His Leu
305                 310                 315                 320

Ser Glu Ile Phe Gly Gln Arg Tyr Arg Leu Ile Val Ser Lys Thr Lys
                325                 330                 335

Asp Leu Ser Gln Asp Asp Cys Cys
            340

<210> SEQ ID NO 5
<211> LENGTH: 327
<212> TYPE: PRT
<213> ORGANISM: Staphylococcus epidermidis

<400> SEQUENCE: 5

Met Val Lys Ser Gly Lys Ala Arg Ala His Thr Asn Ile Ala Leu Ile
1               5                   10                  15

Lys Tyr Trp Gly Lys Ala Asp Glu Thr Tyr Ile Ile Pro Met Asn Asn

-continued

```
            20                  25                  30
Ser Leu Ser Val Thr Leu Asp Arg Phe Tyr Thr Glu Thr Lys Val Thr
        35                  40                  45

Phe Asp Pro Asp Phe Thr Glu Asp Cys Leu Ile Leu Asn Gly Asn Glu
    50                  55                  60

Val Asn Ala Lys Glu Lys Glu Lys Ile Gln Asn Tyr Met Asn Ile Val
65                  70                  75                  80

Arg Asp Leu Ala Gly Asn Arg Leu His Ala Arg Ile Glu Ser Glu Asn
                85                  90                  95

Tyr Val Pro Thr Ala Ala Gly Leu Ala Ser Ser Ala Ser Ala Tyr Ala
            100                 105                 110

Ala Leu Ala Ala Ala Cys Asn Glu Ala Leu Ser Leu Asn Leu Ser Asp
        115                 120                 125

Thr Asp Leu Ser Arg Leu Ala Arg Arg Gly Ser Gly Ser Ala Ser Arg
    130                 135                 140

Ser Ile Phe Gly Gly Phe Ala Glu Trp Glu Lys Gly His Asp Asp Leu
145                 150                 155                 160

Thr Ser Tyr Ala His Gly Ile Asn Ser Asn Gly Trp Glu Lys Asp Leu
                165                 170                 175

Ser Met Ile Phe Val Val Ile Asn Asn Gln Ser Lys Lys Val Ser Ser
            180                 185                 190

Arg Ser Gly Met Ser Leu Thr Arg Asp Thr Ser Arg Phe Tyr Gln Tyr
        195                 200                 205

Trp Leu Asp His Val Asp Glu Asp Leu Asn Glu Ala Lys Glu Ala Val
    210                 215                 220

Lys Asn Gln Asp Phe Gln Arg Leu Gly Glu Val Ile Glu Ala Asn Gly
225                 230                 235                 240

Leu Arg Met His Ala Thr Asn Leu Gly Ala Gln Pro Pro Phe Thr Tyr
                245                 250                 255

Leu Val Gln Glu Ser Tyr Asp Ala Met Ala Ile Val Glu Gln Cys Arg
            260                 265                 270

Lys Ala Asn Leu Pro Cys Tyr Phe Thr Met Asp Ala Gly Pro Asn Val
        275                 280                 285

Lys Val Leu Val Glu Lys Lys Asn Lys Gln Ala Val Met Glu Gln Phe
    290                 295                 300

Leu Lys Val Phe Asp Glu Ser Lys Ile Ile Ala Ser Asp Ile Ile Ser
305                 310                 315                 320

Ser Gly Val Glu Ile Ile Lys
                325

<210> SEQ ID NO 6
<211> LENGTH: 176
<212> TYPE: PRT
<213> ORGANISM: Burkholderia multivorans

<400> SEQUENCE: 6

Met Glu Glu Arg Leu Ile Leu Val Asp Thr Asp Asp Arg Pro Ile Gly
1               5                   10                  15

Ile Cys Glu Lys Met Arg Ala His His Glu Gly Leu Leu His Arg Ala
            20                  25                  30

Phe Ser Ile Phe Val Phe Asp Ser Ala Gly Arg Leu Leu Leu Gln Gln
        35                  40                  45

Arg Ala Leu Asn Lys Tyr His Ser Gly Gly Leu Trp Ser Asn Thr Cys
    50                  55                  60
```

```
Cys Gly His Pro Arg Pro Arg Glu Ala Leu Pro Asp Ala Val Arg Arg
 65                  70                  75                  80

Arg Leu Gly Glu Glu Met Gly Phe Ala Cys Glu Leu Arg Pro Val Asp
                 85                  90                  95

Ala Leu Val Tyr Arg Ala Arg Phe Glu Asn Asp Leu Ile Glu His Glu
            100                 105                 110

Phe Val His Ile His Val Gly Arg Phe Asp Gly Thr Val Ala Pro Asp
        115                 120                 125

Phe Ala Glu Val Ala Ala Trp Arg Trp Ile Asp Val Pro Thr Leu Leu
    130                 135                 140

Glu Trp Met Ala Asp Glu Pro Ser Ala Phe Thr Val Trp Phe His Cys
145                 150                 155                 160

Met Ile Glu Arg Ala Gly Leu Pro Val Leu His Arg Trp Ala His Arg
                165                 170                 175
```

<210> SEQ ID NO 7
<211> LENGTH: 594
<212> TYPE: PRT
<213> ORGANISM: Mucuna pruriens

<400> SEQUENCE: 7

```
Met Ala Thr Asn Pro Ser Cys Leu Ser Thr Pro Phe Leu Ser Ser Thr
  1               5                  10                  15

Pro Ala Leu Ser Thr Arg Phe Pro Leu Ser Glu Asn Phe Thr Gln Lys
                 20                  25                  30

Thr Ser Leu Val Asn Pro Lys Pro Trp Pro Leu Ile Ser Ala Val Ser
             35                  40                  45

Ser Gln Phe Ser Gln Ile Ala Glu Asp Asn Ser Arg Arg Ser Ala Asn
 50                  55                  60

Tyr His Pro Asn Leu Trp Asp Phe Glu Phe Leu Gln Ser Leu Glu Asn
 65                  70                  75                  80

Asp Ser Lys Met Glu Lys Leu Glu Glu Lys Ala Thr Lys Leu Glu Glu
                 85                  90                  95

Glu Val Arg Asn Met Met Asn Glu Ala Lys Thr Glu Ala Leu Ser Leu
            100                 105                 110

Leu Glu Leu Ile Asp Asp Val Gln Arg Leu Gly Leu Thr Tyr Lys Phe
        115                 120                 125

Glu Lys Asp Ile Ile Lys Ala Leu Glu Lys Ile Val Pro Leu Asp Glu
    130                 135                 140

Ser Gly Leu His Val Thr Ser Leu Ser Phe Arg Ile Leu Arg Gln His
145                 150                 155                 160

Gly Phe Glu Val Ser Gln Asp Val Phe Lys Arg Phe Lys Asp Lys Glu
                165                 170                 175

Gly Gly Phe Cys Ala Glu Leu Lys Asp Asp Val Gln Gly Leu Leu Ser
            180                 185                 190

Leu Tyr Glu Ala Ser Tyr Leu Gly Phe Glu Gly Glu Ser Leu Leu Asp
        195                 200                 205

Glu Ala Arg Ala Phe Ser Ile Thr His Leu Lys Asn Asn Leu Asn Lys
    210                 215                 220

Gly Ile Asn Thr Lys Val Ala Gln Gln Val Ser His Ala Leu Glu Leu
225                 230                 235                 240

Pro Tyr His Arg Arg Leu His Arg Leu Glu Ala Arg Trp Leu Leu Asp
                245                 250                 255

Lys Tyr Glu Pro Lys Glu Pro His His His Leu Leu His Glu Leu Ala
            260                 265                 270
```

```
Lys Leu Asp Phe Asn Leu Val Gln Ser Leu Tyr Gln Lys Glu Leu Arg
        275                 280                 285

Glu Leu Ser Leu Trp Trp Arg Glu Ile Gly Leu Thr Ser Lys Leu Asp
    290                 295                 300

Phe Val Arg Asp Arg Leu Met Glu Val Tyr Phe Trp Ala Leu Gly Met
305                 310                 315                 320

Ala Pro Asp Pro Gln Phe Ser Glu Cys Arg Lys Val Val Thr Lys Met
                325                 330                 335

Phe Gly Leu Val Thr Ile Ile Asp Asp Val Tyr Asp Val Tyr Gly Thr
                340                 345                 350

Leu Asp Glu Leu Gln Leu Phe Thr Asp Ala Val Glu Arg Trp Asp Val
        355                 360                 365

Asn Ala Ile Asn Thr Leu Pro Asp Tyr Met Lys Leu Cys Tyr Leu Ala
        370                 375                 380

Leu Tyr Asn Thr Val Asn Asp Thr Ala Tyr Ser Ile Leu Lys Glu Lys
385                 390                 395                 400

Gly His Asn Asn Ile Ser Tyr Leu Thr Lys Ser Trp Cys Glu Leu Cys
                405                 410                 415

Lys Ala Phe Leu Gln Glu Ala Lys Trp Ser Asn Asn Lys Ile Ile Pro
                420                 425                 430

Ala Phe Asn Lys Tyr Leu Asp Asn Ala Ser Val Ser Ser Gly Val
        435                 440                 445

Ala Leu Leu Ala Pro Ser Tyr Phe Leu Val Cys Gln Glu Gln Asp Ile
        450                 455                 460

Ser Asp Gln Ala Leu His Ser Leu Thr Asn Phe His Gly Leu Val Arg
465                 470                 475                 480

Ser Ser Cys Thr Ile Phe Arg Leu Cys Asn Asp Leu Ala Thr Ser Ser
                485                 490                 495

Ala Glu Leu Glu Arg Gly Glu Thr Thr Asn Ser Ile Thr Ser Tyr Met
            500                 505                 510

His Glu Asn Glu Thr Ser Glu Glu Gln Ala Cys Lys Glu Leu Arg Asn
        515                 520                 525

Leu Ile Asp Ala Glu Trp Lys Lys Met Asn Glu Arg Val Ser Asn
        530                 535                 540

Ser Thr Leu Pro Lys Ala Phe Arg Glu Ile Ala Ile Asn Met Ala Arg
545                 550                 555                 560

Ile Ser His Cys Thr Tyr Gln Tyr Gly Asp Gly Leu Gly Arg Pro Asp
                565                 570                 575

Tyr Thr Thr Glu Asn Arg Ile Lys Leu Leu Ile Asp Pro Phe Pro
        580                 585                 590

Ile Asn

<210> SEQ ID NO 8
<211> LENGTH: 1278
<212> TYPE: DNA
<213> ORGANISM: Staphylococcus aureus

<400> SEQUENCE: 8
ctattgttgt ctaatttctt gtaaaatgcg ttcagctact tgtgtattcg cacggggttc      60
ttgcttcaat gcttcagcta cttgcgcaat tcatcacct tttgcaccta caacaatagc    120
taaagattta tattgcaagc tcatatggcc ttgctggata ccttcggaaa cgagcgcgcg    180
acatgctgca aagttctgtg ctaaaccaac ggcagcaact acatgaccta attcttgtgc    240
```

| | |
|---|---|
| tgaatctaca tttagcaatt ctaaagaagc tttagcaatt ggtaatactt ttgtaccacc | 300 |
| gccaacgatt gccaatgtca taggcacttc tattgtacca attaaacgtt gacgttttg | 360 |
| atcgtatctc catgttgcaa taccacgata ctgtccgtca cgactcgcgt atgcatgcgc | 420 |
| acttgcttct gcaccacgcg tatcatttcc tgttgctaaa caacggcat gtatgccatt | 480 |
| cataacacct ttattatgtg ttgcagcacg atgaatatca acttgtgcca atacagaagc | 540 |
| acgttccatt cgtttggcaa cctcttctcc agttctctcg ccccttgcta aatctttaac | 600 |
| gtcaatttcg ccttgaactt taacaacgga cgctgttgca tgattggata aaatactcat | 660 |
| taaaatgtcg ctttgtggag attcattttt taaaaatgca gttatggcct ctaaaatcgt | 720 |
| attaagcata ttagcgccca tagcatcttt cgtatcaaca aatacttta aagatagtaa | 780 |
| ctgttgctca ggaaatgtat caatagctat acgttggtaa ccaccaccac gcgctttaat | 840 |
| agaaggatat gcctcatccg caattttatg aatttgcttt tctaaagctt taatgtctgc | 900 |
| tgataatttt tcagtatcgt caacgccatc aaagacgatt tgacctatca taatacgttc | 960 |
| agaagatacc gttttaaatc cgccagtctg attcactagc tttgcaccat aactagctgc | 1020 |
| agcgacaact gaaggctctt ccaccatcat aggtacaaca tatgccttat cgtccacaat | 1080 |
| gatattcggt aataatccaa cgggtaatgc accttgcgcg atgacatttt caattaaact | 1140 |
| atttgctact tcctcatcaa ttaatggatg attcaataaa atgtcgaatt gatcttctga | 1200 |
| taaccattgc ttatctacca attgttgtaa cttttgttga cgagataaat gtcggaaatt | 1260 |
| cttatctaaa ctttgcat | 1278 |

<210> SEQ ID NO 9
<211> LENGTH: 840
<212> TYPE: DNA
<213> ORGANISM: Staphylococcus aureus

<400> SEQUENCE: 9

| | |
|---|---|
| attgcagtac cgtttaacgc aggtaaaatc aaagttttaa tagaagcctt agagagcggg | 60 |
| aactattcgt ctattaaaag cgatgtttac gatggtatgt tatatgatgc gcctgaccat | 120 |
| cttaagtctt tggtgaaccg ttttgtagaa ttaaataata ttacagagcc gctagcagta | 180 |
| acgatccaaa cgaatttacc accatcacgt ggattaggat cgagtgcagc tgtcgcggtt | 240 |
| gcttttgttc gtgcaagtta tgattttta gggaaatcat taacgaaaga agaactcatt | 300 |
| gaaaaggcta attgggcaga gcaaattgca catggtaaac caagtggtat tgatacgcaa | 360 |
| acgattgtat caggcaaacc agtttggttc caaaaaggtc atgctgaaac attgaaaacg | 420 |
| ttaagtttag acggctatat ggttgttatt gatactggtg tgaaaggttc aacaagacaa | 480 |
| gcggtagaag atgttcataa actttgtgag gatcctcagt acatgtcaca tgtaaaacat | 540 |
| atcggtaagt tagtttacg tgcgagtgat gtgattgaac atcataactt tgaagcccta | 600 |
| gcggatattt ttaatgaatg tcatgcggat ttaaaggcgt tgacagttag tcatgataaa | 660 |
| atagaacaat taatgaaaat tggtaaagaa atggtgcga ttgctggaaa acttactggt | 720 |
| gctggtcgtg gtggaagtat gttattgctt gccaaagatt taccaacagc gaaaaatatt | 780 |
| gtgaaagctg tagaaaaagc tggtgcagca catacatgga ttgagaattt aggaggttaa | 840 |

<210> SEQ ID NO 10
<211> LENGTH: 1077
<212> TYPE: DNA
<213> ORGANISM: Staphylococcus aureus

<400> SEQUENCE: 10

```
atgattcagg tcaaagcacc cggaaaactt tatattgctg agaaatatgc tgtaacagaa      60
ccaggatata aatctgtact tattgcgtta gatcgttttg taactgctac tattgaagaa     120
gcagaccaat ataaaggtac cattcattca aaagcattac atcataaccc agttacattt     180
agtagagatg aagatagtat tgtcatttca gatccacatg cagcaaaaca attaaattat     240
gtggtcacag ctattgaaat atttgaacaa tacgcgaaaa gttgcgatat agcgatgaag     300
cattttcatc tgactattga tagtaattta gatgattcaa atggtcataa atatggatta     360
ggttcaagtg cagcagtact tgtgtcagtt ataaaagtat aaatgaatt ttatgatatg     420 aagttatcta atttatacat ttataaacta gcagtgattg caaatatgaa gttacaaagt     480
ttaagttcat gcggagatat tgctgtgagt gtatatagtg gatggttagc gtatagtact     540
tttgatcatg aatgggttaa gcatcaaatt gaagatacta cggttgaaga gttttaatc      600 aaaaactggc ctggattgca catcgaacca ttacaagcac ctgaaaatat ggaagtactt     660
atcggttgga ctggctcacc ggcgtcatca ccacactttg ttagcgaagt gaaacgtttg     720
aaatcagatc cttcatttta cggtgacttc ttagaagatt cacatcgttg tgttgaaaag     780
cttattcatg cttttaaaac aaataacatt aaaggtgtgc aaaagatggt gcgtcagaat     840
cgtacaatta ttcaacgtat ggataaagaa gctacagttg atatagaaac tgaaaagcta     900
aaatatttgt gtgatattgc tgaaaagtat cacggtgcat ctaaaacatc aggcgctggt     960
ggtggagact gtggtattac aattatcaat aaagatgtag ataaagaaaa aatttatgat    1020
gaatggacaa acatggtat taaaccatta aaatttaata tttatcatgg gcaataa        1077
```

<210> SEQ ID NO 11
<211> LENGTH: 1035
<212> TYPE: DNA
<213> ORGANISM: Streptococcus pneumoniae

<400> SEQUENCE: 11

```
ttgtatcata gccttggtaa ccaatttgac acacgcacaa gaactagcag aaagattaga      60
agagaaagga gctgttcaga catggataga gagcctgtga cagtacgttc ctacgcaaat     120
attgctatta tcaaatattg gggaaagaaa aaagaaaaag atggtgcc tgctactagc      180 agtatttctc taactttgga aaatatgtat acagagacga ccttgtcgcc tttaccagcc     240
aatgtaacag ctgacgaatt ttacatcaat ggtcagctac aaaatgaggt cgagcatgcc     300
aagatgagta agattattga ccgttatcgt ccagctggtg agggctttgt ccgtatcgat     360
actcaaaaca atatgcctac ggcagcgggc ctgtcctcaa gttctagtgg tttgtccgcc     420
ctggtcaagg cttgtaatgc ttatttcaag cttggattgg atagaagtca gttagcgcag     480
gaagccaagt ttgcctcagg ctcttcttct cggagttttt atggaccact aggagcctgg     540
gataaggata gtggagaaat ttaccctgta gagacagact tgaaactagc tatgattatg     600
ttggtgctag aggacaagaa aaaaccaatc tctagccgtg acgggatgaa actttgtgtg     660
gaaacctcga cgactttcga cgactggtt cgtcagtctg agaaggacta tcaggatatg     720
ctgatttatc tcaaggaaaa tgattttgcc aagattggag aattaacgga gaaaatgcc      780 ctggctatgc atgctacgac aaagactgct agtccagcct tttcttatct gacggatgcc     840
tcttatgagg ctatggactt tgttcgtcag cttcgtgaga aggagaggc ctgctacttt      900 accatggatg ctggtcccaa tgttaaggtc ttctgtcagg agaaagactt ggagcatttg     960
tcagaaattt tcggtcagcg ttatcgcttg attgtgtcaa aaacaaagga tttgagtcaa    1020
```

```
gatgattgct gttaa                                                      1035
```

<210> SEQ ID NO 12
<211> LENGTH: 531
<212> TYPE: DNA
<213> ORGANISM: Burkholderia multivorans

<400> SEQUENCE: 12

```
tcatctgtgt gcccagcgat gcagcactgg caatccggct cgctctatca tgcagtggaa      60
ccagacagta aaagcgctcg gctcgtccgc catccactcc agcaaggttg cacatcgat      120
ccatcgccac gccgctactt ccgcgaaatc tggggcgacc gttccatcga accgaccaac    180
atgaatatgc acaaactcgt gctcgatcag gtcgttctca atctcgcgc ggtacacgag    240
cgcgtccacg ggccgaagtt cacatgcgaa tcccatttct cgccaagcc ggcggcgaac      300
cgcatcaggc agcgcttcgc gtggacgcgg gtgcccgcag catgtgttgg accacagccc    360
gcccgagtgg tacttattca gcgcacgctg ctgtagcagc aagcgaccgg ccgagtcgaa    420
cacaaaaatc gagaatgcgc ggtgcagcag cccttcatgg tgcgcgcgca tcttctcgca    480
tattcctatc ggtcgatcgt cggtatcgac gaggatcagg cgttcttcca t            531
```

<210> SEQ ID NO 13
<211> LENGTH: 1785
<212> TYPE: DNA
<213> ORGANISM: Mucuna pruriens

<400> SEQUENCE: 13

```
atggcaacca acccttcatg cttatctact ccatttttgt cctccacacc agcactaagt      60
actagatttc cattaagtga gaacttcaca caaaaaacat ctcttgtcaa tcccaaacct    120
tggccactta tttctgcagt cagctctcaa tttagccaaa tagcagaaga taatagtcgt    180
cgttcagcta attaccaccc aaacctctgg gattttgaat ttctgcagtc tctcgaaaat    240
gactctaaga tggaaaagct ggaagagaaa gcaacaaagt tggaggagga agtgcgaaac    300
atgatgaacg aagcaaagac agaagcacta agcttattgg aattgataga cgacgtccag    360
cgtctgggat tgacctacaa gtttgagaag gacataatca aagcccttga gaagattgtt    420
ccattggatg agagtgggct gcatgttact tctctcagct ccgtatact agacaacat      480
ggctttgagg tttcccaaga tgtgtttaag agatttaagg acaaggaggg aggttttgt     540
gctgaactta agacgatgt tcaagggttg ctaagtctat atgaagcatc ctatcttggt    600
tttgagggag aaagtctctt agacgaggca agggcatttt caataacaca tctcaagaac    660
aacctaaaca aggaataaaa caccaaagta gcccaacaag ttagccatgc actggaactt    720
ccttatcatc gaagactgca tagactgaa gcacgatggc tccttgacaa atatgaacca     780
aaggaaccccc accatcattt actacacgag cttgcaaagt tggatttcaa tttggtccaa    840
tcattgtacc agaaagagtt gcgagaattg tcactgtggt ggagggagat tgggctcaca    900
agcaagttgg actttgttcg agacagatta atggaagtgt acttttgggc gctgggaatg     960
gcacctgatc ctcaatttag tgaatgtcgt aaagtcgtca ctaaaatgtt tgggctagtt    1020
actatcatcg atgatgtata tgacgtttac ggtactttgg acgagctaca actcttcacc    1080
gatgctgttg agagatggga cgtgaatgcg ataaatacac ttccagacta tatgaaattg    1140
tgctatttag ccctttataa caccgtcaat gacacagctt atagcatcct taaagaaaag    1200
ggacataaca acatttctta tttgacaaaa tcttggtgtg agttgtgcaa agcattcctc    1260
caagaagcaa aatggtcaaa caacaaaatc attccagcat tcaacaagta cctagacaat    1320
```

```
gcatcggtgt cctcctctgg tgtggctttg cttgctcctt cctacttctt agtgtgccaa    1380
gaacaagaca tttcagacca agctcttcat tccttaacta atttccatgg ccttgtgcgt    1440
tcatcatgca ccatttttag gctttgcaat gatctggcta cctcatcggc tgagctagag    1500
agaggtgaaa caacaaattc aatcacatcg tacatgcatg agaatgagac ttctgaggag    1560
caagcatgta aggagttgag aaatttgatc gatgcagagt ggaagaagat gaatgaagag    1620
cgagtttcaa attctacact cccaaaagca tttagggaaa tagctattaa catggctcgg    1680
atttcccatt gcacatacca atatggagac ggacttggaa ggcccgacta caccacagag    1740
aacaggataa agttgctact aatagaccct tttccaatta attag                    1785
```

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 14

His His His His His His
1               5

METHODS, CELLS AND REAGENTS FOR PRODUCTION OF ISOPRENE, DERIVATIVES AND INTERMEDIATES THEREOF

This application claims priority to U.S. Provisional Patent Application No. 62/205,926, filed Aug. 17, 2015.

SEQUENCE LISTING

The instant application contains a Sequence Listing which has been submitted electronically in ASCII format and is hereby incorporated by reference in its entirety. Said ASCII copy, created on Jul. 26, 2016, is named 12444_0582-00000_SL.txt and is 31,431 bytes in size.

TECHNICAL FIELD

This application relates to methods for biosynthesizing 3-hydroxy-3-methylglutaryl-coA (3-HMG) and intermediates thereof, using one or more isolated enzymes such as one or more of a 4-methyl-2-oxopentanoate, a 3-methylbutanoyl-CoA oxidoreductase, a 3-methylbut-2-enoyl-CoA carboxylase, and a 3-methylglutaconyl-CoA hydratase; or using non-naturally occurring host cells expressing one or more such enzymes.

This application further relates to methods for biosynthesizing isoprene and intermediates thereof from 3-hydroxy-3-methylglutaryl-coA using one or more isolated enzymes, such as one or more of a hydroxymethylglutaryl Co-A reductase, a mevalonate-kinase, a phosphomevalonate kinase, a diphosphomevalonate decarboxylase, an isopentenyl diphosphate isomerase, and an isoprene synthase; or using non-naturally occurring host cells expressing one or more such enzymes.

BACKGROUND

Isoprene is an important monomer for the production of specialty elastomers including motor mounts/fittings, surgical gloves, rubber bands, golf balls and shoes. Styrene-isoprene-styrene block copolymers form a key component of hot-melt pressure-sensitive adhesive formulations and cis-poly-isoprene is utilized in the manufacture of tires (Whited et al., Industrial Biotechnology, 2010, 6(3), 152-163).

Manufacturers of rubber goods depend on either imported natural rubber from the Brazilian rubber tree or petroleum-based synthetic rubber polymers (Whited et al., 2010, supra). Given a reliance on petrochemical feedstocks and the harvesting of trees, biotechnology offers an alternative approach via biocatalysis. Biocatalysis is the use of biological catalysts, such as enzymes, to perform biochemical transformations of organic compounds.

Accordingly, against this background, it is clear that there is a need for sustainable methods for producing intermediates, in particular isoprene, wherein the methods are biocatalysis based.

Both bioderived feedstocks and petrochemical feedstocks are viable starting materials for the biocatalysis processes. The introduction of vinyl groups into medium carbon chain length enzyme substrates is a key consideration in synthesizing isoprene via biocatalysis processes.

There are known metabolic pathways leading to the synthesis of isoprene in prokaryotes such as *Bacillis subtillis* and eukaryotes such as *Populus alba* (Whited et al., 2010, supra).

Isoprene may be synthesized via two routes leading to the precursor dimethylvinyl-PP, such as the mevalonate and the non-mevalonate pathway (Kuzuyama, Biosci. Biotechnol. Biochem., 2002, 66(8), 1619-1627).

The mevaionate pathway incorporates a decarboxylase enzyme, mevalonate diphosphate decarboxylase (hereafter Mdd), that introduces the first vinyl-group into the precursors leading to isoprene. The second vinyl-group is introduced by isoprene synthase (hereafter IspS) in the final step in synthesizing isoprene.

The mevalonate pathway (shown in part in FIG. 2) has been exploited in the biocatalytic production of isoprene using *E. coli* as host. *E. coli* engineered with the mevalonate pathway requires three moles of acetyl-CoA, three moles of ATP and two moles of NAD(P)H to produce a mole of isoprene. Given a theoretical maximum yield of 25.2% (w/w) for the mevalonate pathway, isoprene has been produced biocatalytically at a volumetric productivity of 2 g/(L·h) with a yield of 11% (w/w) from glucose (Whited et al., 2010, supra). Particularly, the phosphate activation of mevalonate to 5-diphosphomevalonate is energy intensive metabolically, requiring two moles of ATP per mole of isoprene synthesis (FIG. 2). Accordingly, reducing the ATP consumption can improve the efficiency of the pathway.

SUMMARY

The inventors have determined that it is possible to biosynthesize 3-HMG and/or intermediates thereof from 4-methyl-2-oxopentanoate using one or more isolated enzymes, or using non-naturally occurring host cells expressing one or more such enzymes. For example, 3-HMG may be biosynthesized from 4-methyl-2-oxopentanoate using one or more of a 4-methyl-2-oxopentanoate dehydrogenase, a 3-methylbutanoyl-CoA oxidoreductase, a 3-methylbut-2-enoyl-CoA carboxylase, and a 3-methylglutaconyl-CoA hydratase. For further example, 3-HMG may be biosynthesized from 4-methyl-2-oxopentanoate using one or more of a 4-methyl-2-oxopentanoate decarboxylase, a 3-methylbutanal dehydrogenase, a 3-methylbutanoate-CoA ligase, a 3-methylbutanoyl-CoA oxidoreductase, a 3-methylbut-2-enoyl-CoA carboxylase, and a 3-methylglutaconyl-CoA hydratase.

In one embodiment, are methods, including non-naturally occurring methods, for synthesizing 3-HMG, comprising enzymatically converting 4-methyl-2-oxopentanoate to 3-methylbutanoyl-CoA using a polypeptide having the activity of an EC 1.2.7.7 or EC 1.2.1.-enzyme, enzymatically converting 3-methylbutanoyl-CoA to 3-methylbut-2-enoyl-CoA using a polypeptide having the activity of an EC 1.3.8.4 enzyme, enzymatically converting 3-methylbut-2-enoyl-CoA to 3-methyl-glutaconyl—using a polypeptide having the activity of an EC 6.4.1.4 enzyme, and enzymatically converting 3-methyl-glutaconyl-CoA to 3-hydroxy-3-methylglutaryl-CoA using a polypeptide having the activity of an EC 4.2.1.18 enzyme.

In one embodiment, are methods, including non-naturally occurring methods, for synthesizing 3-HMG, comprising enzymatically converting 4-methyl-2-oxopentanoate to 3-methylbutanal using a polypeptide having the activity of an EC 4.1.1.74 or EC 4.1.1.43 enzyme, enzymatically converting 3-methylbutanal to 3-methylbutanoate using a polypeptide having the activity of an EC 1.2.1.39 or EC 1.2.1.5 enzyme, enzymatically converting 3-methylbutanoate to 3-methylbutanoyl-CoA using a polypeptide having the activity of an EC 6.2.1.2 enzyme, enzymatically converting 3-methylbutanoyl-CoA to 3-methylbut-2-enoyl-CoA using a polypeptide having the activity of an EC 1.3.8.4 enzyme, enzymatically converting 3-methylbut-2-enoyl-CoA to 3-methyl-glutaconyl—using a polypeptide having the activity of an EC 6.4.1.4 enzyme, and enzymatically converting 3-methyl-glutaconyl-CoA to 3-hydroxy-3-methylglutaryl-CoA using a polypeptide having the activity of an EC 4.2.1.18 enzyme.

The inventors have also determined that it is possible to biosynthesize isoprene and/or intermediates thereof from 4-methyl-2-oxopentanoate via a 3-HMG intermediate using one or more isolated enzymes, or using non-naturally occurring host cells expressing one or more such enzymes. For example, isoprene may be synthesized from 4-methyl-2-oxopentanoate using one or more of a 4-methyl-2-oxopentanoate dehydrogenase, a 3-methylbutanoyl-CoA oxidoreductase, a 3-methylbut-2-enoyl-CoA carboxylase, a 3-methylglutaconyl-CoA hydratase, a hydroxymethylglutaryl Co-A reductase, a mevalonate-kinase, a phosphomevalonate kinase, a diphosphomevalonate decarboxylase, an isopentenyl diphosphate isomerase, and an isoprene synthase. For further example, isoprene may be biosynthesized from 4-methyl-2-oxopentanoate using one or more of a 4-methyl-2-oxopentanoate decarboxylase, a 3-methylbutanal dehydrogenase, a 3-methylbutanoate-CoA ligase, a 3-methylbutanoyl-CoA oxidoreductase, a 3-methylbut-2-enoyl-CoA carboxylase, a 3-methylglutaconyl-CoA hydratase, a hydroxymethylglutaryl Co-A reductase, a mevalonate-kinase, a phosphomevalonate kinase, a diphosphomevalonate decarboxylase, an isopentenyl diphosphate isomerase, and an isoprene synthase.

In one embodiment, are methods, including non-naturally occurring methods, for synthesizing isoprene via a 3-HMG intermediate, comprising enzymatically converting 4-methyl-2-oxopentanoate to 3-methylbutanoyl-CoA using a polypeptide having the activity of an EC 1.2.7.7 or EC 1.2.1.-enzyme, enzymatically converting 3-methylbutanoyl-CoA to 3-methylbut-2-enoyl-CoA using a polypeptide having the activity of an EC 1.3.8.4 enzyme, enzymatically converting 3-methylbut-2-enoyl-CoA to 3-methyl-glutaconyl—using a polypeptide having the activity of an EC 6.4.1.4 enzyme, enzymatically converting 3-methyl-glutaconyl-CoA to 3-hydroxy-3-methylglutaryl-CoA using a polypeptide having the activity of an EC 4.2.1.18 enzyme, enzymatically converting 3-hydroxy-3-methylglutaryl-CoA to (R)-mevalonate using a polypeptide having the activity of an EC 1.1.1.34 enzyme, enzymatically converting (R)-mevalonate to (R)-5-phosphomevalonate using a polypeptide having the activity of an EC 2.7.1.36 enzyme, enzymatically converting (R)-5-phosphomevalonate to (R)-5-diphosphomevalonate using a polypeptide having the activity of an EC 2.7.4.2 enzyme, enzymatically converting (R)-5-diphosphomevalonate to isopentenyl diphosphate using a polypeptide having the activity of an EC 4.1.1.33 enzyme, enzymatically converting isopentenyl diphosphate to dimethylallyl diphosphate using a polypeptide having the activity of an EC 5.3.3.2 enzyme, and enzymatically converting dimethylallyl diphosphate to isoprene using a polypeptide having the activity of an EC 4.2.3.27 enzyme.

In one embodiment, are methods, including non-naturally occurring methods, for synthesizing isoprene via a 3-HMG intermediate, comprising enzymatically converting 4-methyl-2-oxopentanoate to 3-methylbutanal using a polypeptide having the activity of an EC 4.1.1.74 or EC 4.1.1.43 enzyme, enzymatically converting 3-methylbutanal to 3-methylbutanoate using a polypeptide having the activity of an EC 1.2.1.39 or EC 1.2.1.5 enzyme, enzymatically converting 3-methylbutanoate to 3-methylbutanoyl-CoA using a polypeptide having the activity of an EC 6.2.1.2 enzyme, enzymatically converting 3-methylbutanoyl-CoA to 3-methylbut-2-enoyl-CoA using a polypeptide having the activity of an EC 1.3.8.4 enzyme, enzymatically converting 3-methylbut-2-enoyl-CoA to 3-methyl-glutaconyl—using a polypeptide having the activity of an EC 6.4.1.4 enzyme, enzymatically converting 3-methyl-glutaconyl-CoA to 3-hydroxy-3-methylglutaryl-CoA using a polypeptide having the activity of an EC 4.2.1.18 enzyme, enzymatically converting 3-hydroxy-3-methylglutaryl-CoA to (R)-mevalonate using a polypeptide having the activity of an EC 1.1.1.34 enzyme, enzymatically converting (R)-mevalonate to (R)-5-phosphomevalonate using a polypeptide having the activity of an EC 2.7.1.36 enzyme, enzymatically converting (R)-5-phosphomevalonate to (R)-5-diphosphomevalonate using a polypeptide having the activity of an EC 2.7.4.2 enzyme, enzymatically converting (R)-5-diphosphomevalonate to isopentenyl diphosphate using a polypeptide having the activity of an EC 4.1.1.33 enzyme, enzymatically converting isopentenyl diphosphate to dimethylallyl diphosphate using a polypeptide having the activity of an EC 5.3.3.2 enzyme, and enzymatically converting dimethylallyl diphosphate to isoprene using a polypeptide having the activity of an EC 4.2.3.27 enzyme.

In one embodiment, are methods, including non-naturally occurring methods, for synthesizing isoprene via a 3-HMG intermediate, comprising enzymatically converting 3-hydroxy-3-methylglutaryl-CoA to (R)-mevalonate using a hydroxymethylglutaryl Co-A reductase enzyme, for example a hydroxymethylglutaryl Co-A reductase having the amino acid sequence set forth in SEQ ID No: 1 or a functional fragment thereof; enzymatically converting (R)-mevalonate to (R)-5-phosphomevalonate using a mevalonate-kinase enzyme, for example a mevalonate-kinase having the amino acid sequence set forth in SEQ ID No: 2 or a functional fragment thereof; enzymatically converting (R)-5-phosphomevalonate to (R)-5-diphosphomevalonate using a phosphomevalonate kinase enzyme, for example a phosphomevalonate kinase having the amino acid sequence set forth in SEQ ID No: 3 or a functional fragment thereof; enzymatically converting (R)-5-diphosphomevalonate to isopentenyl diphosphate using a diphosphomevalonate decarboxylase enzyme, for example a diphosphomevalonate decarboxylase having the amino acid sequence set forth in SEQ ID No: 4 or a functional fragment thereof, or a diphosphomevalonate decarboxylase having the amino acid sequence set forth in SEQ ID No: 5 or a functional fragment thereof; enzymatically converting isopentenyl diphosphate to dimethylallyl diphosphate using an isopentenyl diphosphate isomerase, for example an isopentenyl diphosphate isomerase having the amino acid sequence set forth in SEQ ID No: 6 or a functional fragment thereof; and enzymatically converting dimethylallyl diphosphate to isoprene using an isoprene synthase enzyme, for example an isoprene synthase having the amino acid sequence set forth in SEQ ID No: 7 or a functional fragment thereof.

In one embodiment, the methods for synthesizing 3-HMG from 4-methyl-2-oxopentanoate and for synthesizing isoprene from 4-methyl-2-oxopentanoate via a 3-HMG intermediate are performed in a non-naturally occurring host, which may be a prokaryotic or eukaryotic host.

In one embodiment, at least one of the enzymatic conversions within the methods for synthesizing 3-HMG from 4-methyl-2-oxopentanoate and for synthesizing isoprene from 4-methyl-2-oxopentanoate via a 3-HMG intermediate is performed in a non-naturally occurring host, which may be a prokaryotic or eukaryotic host.

In one embodiment, are non-naturally occurring hosts capable of synthesizing 3-HMG from 4-methyl-2-oxopentanoate, said host comprising at least one exogenous nucleic acid encoding a polypeptide having the activity of an EC 1.2.7.7 or EC 1.2.1.-enzyme, at least one exogenous nucleic acid encoding a polypeptide having the activity of an EC 1.3.8.4 enzyme, at least one exogenous nucleic acid encoding a polypeptide having the activity of an EC 6.4.1.4 enzyme; and at least one exogenous nucleic acid encoding a polypeptide having the activity of an EC 4.2.1.18 enzyme.

In one embodiment, are non-naturally occurring hosts capable of synthesizing 3-HMG from 4-methyl-2-oxopentanoate, said host comprising at least one exogenous nucleic acid encoding a polypeptide having the activity of an EC 4.1.1.74 or EC 4.1.1.43 enzyme, at least one exogenous nucleic acid encoding a polypeptide having the activity of an EC 1.2.1.39 or EC 1.2.1.5 enzyme, at least one exogenous nucleic acid encoding a polypeptide having the activity of an EC 6.2.1.2. enzyme, at least one exogenous nucleic acid encoding a polypeptide having the activity of an EC 1.3.8.4 enzyme, at least one exogenous nucleic acid encoding a polypeptide having the activity of an EC 8.4.1.4 enzyme, and at least one exogenous nucleic acid encoding a polypeptide having the activity of an EC 4.2.1.18 enzyme.

In one embodiment, are non-naturally occurring hosts capable of synthesizing 3-HMG from 4-methyl-2-oxopentanoate via both of the pathways disclosed above. In one embodiment, are non-naturally occurring hosts capable of synthesizing 3-HMG from 4-methyl-2-oxopentanoate via simultaneous operation of both of the pathways disclosed above.

In one embodiment, are non-naturally occurring hosts capable of synthesizing isoprene from 4-methyl-2-oxopentanoate via a 3-HMG intermediate, said host comprising at least one exogenous nucleic acid encoding a polypeptide having the activity of an EC 1.2.7.7 or EC 1.2.1.-enzyme, at least one exogenous nucleic acid encoding a polypeptide having the activity of an EC 1.3.8.4 enzyme, at least one exogenous nucleic acid encoding a polypeptide having the activity of an EC 8.4.1.4 enzyme, at least one exogenous nucleic acid encoding a polypeptide having the activity of an EC 4.2.1.18 enzyme, at least one exogenous nucleic acid encoding a polypeptide having the activity of an EC 1.1.1.34 enzyme, at least one exogenous nucleic acid encoding a polypeptide having the activity of an EC 2.7.1.36 enzyme, at least one exogenous nucleic acid encoding a polypeptide having the activity of an EC 2.7.4.2 enzyme, at least one exogenous nucleic acid encoding a polypeptide having the activity of an EC 4.1.1.33 enzyme, at least one exogenous nucleic acid encoding a polypeptide having the activity of an EC 5.3.3.2 enzyme, and least one exogenous nucleic acid encoding a polypeptide having the activity of an EC 4.2.3.27 enzyme.

In one embodiment, are non-naturally occurring hosts capable of synthesizing isoprene from 4-methyl-2-oxopentanoate via a 3-HMG intermediate, said host comprising at least one exogenous nucleic acid encoding a polypeptide having the activity of an EC 4.1.1.74 or EC 4.1.1.43 enzyme, at least one exogenous nucleic acid encoding a polypeptide having the activity of an EC 1.2.1.39 or EC 1.2.1.5 enzyme, at least one exogenous nucleic acid encoding a polypeptide having the activity of an EC 6.2.1.2. enzyme, at least one exogenous nucleic acid encoding a polypeptide having the activity of an EC 1.3.8.4 enzyme, at least one exogenous nucleic acid encoding a polypeptide having the activity of an EC 6.4.1.4 enzyme, at least one exogenous nucleic acid encoding a polypeptide having the activity of an EC 4.2.1.18 enzyme, at least one exogenous nucleic acid encoding a polypeptide having the activity of an EC 1.1.1.34 enzyme, at least one exogenous nucleic acid encoding a polypeptide having the activity of an EC 2.7.1.36 enzyme, at least one exogenous nucleic acid encoding a polypeptide having the activity of an EC 2.7.4.2 enzyme, at least one exogenous nucleic acid encoding a polypeptide having the activity of an EC 4.1.1.33 enzyme, at least one exogenous nucleic acid encoding a polypeptide having the activity of an EC 5.3.3.2 enzyme, and least one exogenous nucleic acid encoding a polypeptide having the activity of an EC 4.2.3.27 enzyme.

In one embodiment, are non-naturally occurring hosts capable of synthesizing isoprene from 4-methyl-2-oxopentanoate via a 3-HMG intermediate via both of the pathways disclosed above. In one embodiment, are non-naturally occurring hosts capable of synthesizing isoprene from 4-methyl-2-oxopentanoate via a 3-HMG intermediate via simultaneous operation of both of the pathways disclosed above.

In one embodiment, hosts may be capable of endogenously producing isoprene, for example via a non-mevalonate pathway.

In one embodiment, at least one of the enzymatic conversions of the methods comprises gas fermentation, for example fermentation of at least one of natural gas, syngas, $CO_2/H_2$, methanol, ethanol, non-volatile residue, caustic wash from cyclohexane oxidation processes, or waste stream from a chemical or petrochemical industry.

Methods described herein can be performed using isolated enzymes.

Methods described herein can be performed using cell lysates comprising the enzymes.

Methods described herein can be performed in a non-naturally occurring host, such as a recombinant host. For example, the host can be a prokaryote selected from the group consisting of the genus *Escherichia* such as *Escherichia coli*; from the genus *Clostridia* such as *Clostridium ljungdahlii*, *Clostridium autoethanogenum* or *Clostridium kluyveri*, from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens* or *Pseudomonas putida*: from the genus *Bacillus* such as *Bacillus subtillis*; or from the genus *Rhodococcus* such as *Rhodococcus equi*. The host can be a eukaryote, for example a eukaryote selected from the group consisting of the genus *Aspergillus* such as *Aspergillus niger*, from the genus *Saccharomyces* such as *Saccharomyces cerevisiae*; from the genus *Pichia* such as *Pichia pastoris*; from the genus *Yarrowia* such as *Yarrowia lipolytica*; from the genus *Issatchenkia* such as *Issatchenkia orientalis*; from the genus *Debaryomyces* such as *Debaryomyces hansenii*, from the genus *Arxula* such as *Arxula adeninivorans*; or from the genus *Kluyveromyces* such as *Kluyveromyces lactis*. The host can be a prokaryotic or eukaryotic chemolithotroph.

The host can be subjected to a fermentation strategy entailing anaerobic, micro-aerobic or aerobic cultivation. A cell retention strategy using a ceramic hollow fiber membrane can be employed to achieve and maintain a high cell density during fermentation.

The principal carbon source fed to the fermentation can derive from a biological or a non-biological feedstock. The biological feedstock can be, or can derive from, monosaccharides, disaccharides, hemicellulose such as levulinic acid and furfural, cellulose, lignocellulose, lignin, triglycerides such as glycerol and fatty acids, agricultural waste or municipal waste. The non-biological feedstock can be, or can derive from, either natural gas, syngas, $CO_2/H_2$, methanol, ethanol, non-volatile residue (NVR), caustic wash from cyclohexane oxidation processes or other waste stream from either the chemical or petrochemical industries.

The reactions of the pathways described herein can be performed in one or more cell (e.g., host cell) strains (a) naturally expressing one or more relevant enzymes, (b) genetically engineered to express one or more relevant enzymes, or (c) naturally expressing one or more relevant enzymes and genetically engineered to express one or more relevant enzymes. Alternatively, relevant enzymes can be extracted from any of the above types of host cells and used in a purified or semi-purified form. Extracted enzymes can optionally be immobilized to a solid substrate such as the floors and/or walls of appropriate reaction vessels. Moreover, such extracts include lysates (e.g., cell lysates) that can be used as sources of relevant enzymes. In the methods provided by this application, all the steps can be performed in cells (e.g., host cells), all the steps can be performed using extracted enzymes, or some of the steps can be performed in cells and others can be performed using extracted enzymes.

Unless otherwise defined, all technical and scientific terms used herein have the same meaning as commonly understood by one of ordinary skill in the art to which this application pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features, objects, and advantages will be apparent from the description and the drawings, and from the claims. The word "comprising" in the claims may be replaced by "consisting essentially of" or with "consisting of," according to standard practice in patent law.

DESCRIPTION OF DRAWINGS

FIG. 3A and FIG. 3B contain the amino acid sequences of enzymes which may be used for biosynthesizing isoprene from 3-HMG via the mevalonate pathway.

FIG. 4A, FIG. 4B, FIG. 4C, and FIG. 4D contain nucleic acid sequences encoding enzymes which may be used for biosynthesizing isoprene from 3-HMG via the mevalonate pathway.

DETAILED DESCRIPTION

Figure 1:
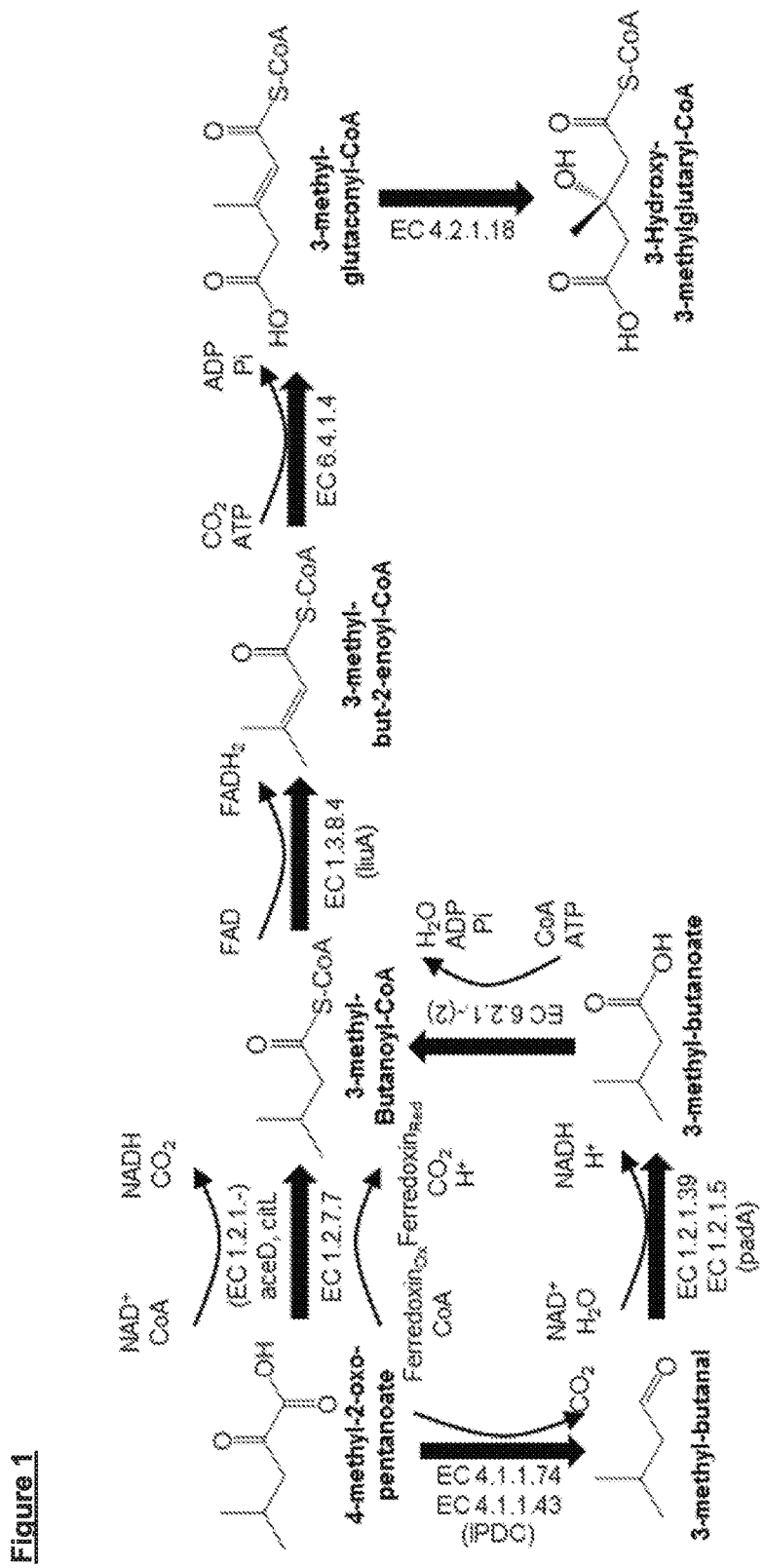
FIG. 1 is a schematic of an exemplary biochemical pathway leading to 3-HMG from 4-methyl-2-oxopentanoate.

In one aspect are provided enzymes and non-naturally occurring, for example recombinant, host microorganisms for synthesis of 3-HMG from 4-methyl-2-oxopentanoate, and/or intermediates thereof, in one or more enzymatic steps.

In one aspect are provided enzymes and non-naturally occurring, for example recombinant, host microorganisms for synthesis of isoprene from 4-methyl-2-oxopentanoate, and/or intermediates thereof, via a 3-HMG intermediate in one or more enzymatic steps.

In one aspect are provided enzymes and non-naturally occurring recombinant host microorganisms for synthesis of 3-HMG from 4-methyl-2-oxopentanoate, and/or intermediates, in one or more enzymatic steps comprising use of one or more of a 4-methyl-2-oxopentanoate dehydrogenase, a 3-methylbutanoyl-CoA oxidoreductase, a 3-methylbut-2-enoyl-CoA carboxylase, and a 3-methylglutaconyl-CoA hydratase; or using non-naturally occurring host cells expressing one or more such enzymes. In a further aspect are provided enzymes and non-naturally occurring recombinant host microorganisms for synthesis of 3-HMG from 4-methyl-2-oxopentanoate, and/or intermediates, in one or more enzymatic steps comprising use of one or more of a 4-methyl-2-oxopentanoate decarboxylase, a 3-methylbutanal dehydrogenase, a 3-methylbutanoate-CoA ligase, a 3-methylbutanoyl-CoA oxidoreductase, a 3-methylbut-2-enoyl-CoA carboxylase, and a 3-methylglutaconyl-CoA hydratase; or using non-naturally occurring host cells expressing one or more such enzymes.

In one aspect are provided enzymes and non-naturally occurring recombinant host microorganisms for synthesis of isoprene and/or intermediates thereof via a 3-HMG intermediate in one or more enzymatic steps comprising use of one or more of a 4-methyl-2-oxopentanoate dehydrogenase, a 3-methylbutanoyl-CoA oxidoreductase, a 3-methylbut-2-enoyl-CoA carboxylase, a 3-methylglutaconyl-CoA hydratase, a hydroxymethylglutaryl Co-A reductase, a mevalonate-kinase, a phosphomevalonate kinase, a diphosphomevalonate decarboxylase, an isopentenyl diphosphate isomerase, and an isoprene synthase; or using non-naturally occurring host cells expressing one or more such enzymes. In a further aspect are provided enzymes and non-naturally occurring recombinant host microorganisms for synthesis of isoprene and/or intermediates thereof via a 3-HMG intermediate in one or more enzymatic steps comprising use of one or more of a 4-methyl-2-oxopentanoate decarboxylase, a 3-methylbutanal dehydrogenase, a 3-methylbutanoate-CoA ligase, a 3-methylbutanoyl-CoA oxidoreductase, a 3-methylbut-2-enoyl-CoA carboxylase, a 3-methylglutaconyl-CoA hydratase, a hydroxymethylglutaryl Co-A reductase, a mevalonate-kinase, a phosphomevalonate kinase, a diphosphomevalonate decarboxylase, an isopentenyl diphosphate isomerase, and an isoprene synthase; or using non-naturally occurring host cells expressing one or more such enzymes.

Host microorganisms described herein can include pathways that can be manipulated such that isoprene or its intermediates can be produced. In an endogenous pathway, the host microorganism naturally expresses all of the enzymes catalyzing the reactions within the pathway. A host microorganism containing an engineered pathway does not naturally express all of the enzymes catalyzing the reactions within the pathway but has been engineered such that all of the enzymes within the pathway are expressed in the host.

The term "exogenous" as used herein with reference to a nucleic acid (or a protein) and a host refers to a nucleic acid that does not occur in (and cannot be obtained from) a cell of that particular type as it is found in nature or a protein encoded by such a nucleic acid. Thus, a non-naturally-occurring nucleic acid is considered to be exogenous to a host once in the host. It is important to note that non-naturally-occurring nucleic acids can contain nucleic acid subsequences or fragments of nucleic acid sequences that are found in nature provided the nucleic acid as a whole does not exist in nature. For example, a nucleic acid molecule containing a genomic DNA sequence within an expression vector is non-naturally occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., gDNA or genomic DNA) in an arrangement not found in nature is non-naturally-occurring nucleic acid. A nucleic acid that is naturally-occurring can be exogenous to a particular host microorganism. For example, an entire chromosome isolated from a cell of yeast x is an exogenous nucleic acid with respect to a cell of yeast y once that chromosome is introduced into a cell of yeast y.

In contrast, the term "endogenous" as used herein with reference to a nucleic acid (e.g., a gene) (or a protein) and a host refers to a nucleic acid (or protein) that does occur in (and can be obtained from) that particular host as it is found in nature. Moreover, a cell "endogenously expressing" a nucleic acid (or protein) expresses that nucleic acid (or protein) as does a host of the same particular type as it is found in nature. Moreover, a host "endogenously producing" or that "endogenously produces" a nucleic acid, protein, or other compound produces that nucleic acid, protein, or compound as does a host of the same particular type as it is found in nature.

For example, depending on the host and the compounds produced by the host, one or more of the following enzymes may be expressed in the host: a 4-methyl-2-oxopentanoate dehydrogenase, a 4-methyl-2-oxopentanoate decarboxylase, a 3-methylbutanal dehydrogenase, a 3-methylbutanoate-CoA ligase, a 3-methylbutanoyl-CoA oxidoreductase, a 3-methylbut-2-enoyl-CoA carboxylase, a 3-methylglutaconyl-CoA hydratase, a hydroxymethylglutaryl Co-A reductase, a mevalonate-kinase, a phosphomevalonate kinase, a diphosphomevalonate decarboxylase, an isopentenyl diphosphate isomerase, and an isoprene synthase.

As used herein, the term "mevalonate pathway" refers to a pathway for synthesis of isoprene comprising enzymatically converting 3-hydroxy-3-methylglutaryl-CoA to (R)-mevalonate using a hydroxymethylglutaryl Co-A reductase; enzymatically converting (R)-mevalonate to (R)-5-phosphomevalonate using a mevalonate-kinase enzyme; enzymatically converting (R)-5-phosphomevalonate to (R)-5-diphosphomevalonate using a phosphomevalonate kinase enzyme; enzymatically converting (R)-5-diphosphomevalonate to isopentenyl diphosphate using a diphosphomevalonate decarboxylase enzyme; enzymatically converting isopentenyl diphosphate to dimethylallyl diphosphate using an isopentenyl diphosphate isomerase; and enzymatically converting dimethylallyl diphosphate to isoprene using an isoprene synthase enzyme.

In one embodiment the 4-methyl-2-oxopentanoate dehydrogenase is the gene product of aceD. In one embodiment the 4-methyl-2-oxopentanoate dehydrogenase is the gene product of citL. In one embodiment the 4-methyl-2-oxopentanoate dehydrogenase is classified under EC 1.2.1-. In one embodiment the 4-methyl-2-oxopentanoate dehydrogenase has the activity of an enzyme classified under EC 1.2.1-. In one embodiment the 4-methyl-2-oxopentanoate dehydrogenase is classified under EC 1.2.7.7. In one embodiment the 4-methyl-2-oxopentanoate dehydrogenase has the activity of an enzyme classified under EC 1.2.7.7.

In one embodiment the 4-methyl-2-oxopentanoate decarboxylase is the gene product of ipdC. In one embodiment the 4-methyl-2-oxopentanoate decarboxylase is classified under EC 4.1.1.74. In one embodiment the 4-methyl-2-oxopentanoate decarboxylase has the activity of an enzyme classified under EC 4.1.1.74. In one embodiment the 4-methyl-2-oxopentanoate decarboxylase is classified under EC 4.1.1.43. In one embodiment the 4-methyl-2-oxopentanoate decarboxylase has the activity of an enzyme classified under EC 4.1.1.43.

In one embodiment the 3-methylbutanal dehydrogenase is the gene product of padA. In one embodiment the 3-methylbutanal dehydrogenase is classified under EC 1.2.1.39. In one embodiment the 3-methylbutanal dehydrogenase has the activity of an enzyme classified under EC 1.2.1.39. In one embodiment the 3-methylbutanal dehydrogenase is classified under EC 1.2.1.5. In one embodiment the 3-methylbutanal dehydrogenase has the activity of an enzyme classified under EC 1.2.1.5.

In one embodiment the 3-methylbutanoate-CoA ligase is classified under EC 6.2.1.-. In one embodiment the 3-methylbutanoate-CoA ligase is classified under EC 6.2.1.2.

In one embodiment the 3-methylbutanoyl-CoA oxidoreductase is the gene product of liuA. In one embodiment 3-methylbutanoyl-CoA oxidoreductase is classified under EC 1.3.8.4.

In one embodiment the 3-methylbut-2-enoyl-CoA carboxylase is classified under EC 6.4.1.4.

In one embodiment the 3-methylglutaconyl-CoA hydratase is classified under EC 4.2.1.18.

In one embodiment the hydroxymethylglutaryl Co-A reductase is the gene product of mvaA. In one embodiment the hydroxymethylglutaryl Co-A reductase is classified under EC 1.1.1.34. In one embodiment the hydroxymethylglutaryl Co-A reductase is a *Staphylococcus aureus* hydroxymethylglutaryl Co-A reductase (Genbank Accession No. BAB58707.1 SEQ ID No: 1). See FIG. 3A. In one embodiment the hydroxymethylglutaryl Co-A reductase is a *Staphylococcus aureus* hydroxymethylglutaryl Co-A reductase encoded by a nucleic acid having the sequence set forth in SEQ ID No: 8. See FIG. 4A.

In one embodiment the mevalonate-kinase is the gene product of mvak1. In one embodiment the mevalonate-kinase is classified under EC 2.7.1.38. In one embodiment the mevalonate-kinase is a *Staphylococcus aureus* mevalonate-kinase (Genbank Accession No. BAB58752.1, SEQ ID No: 2). See FIG. 3A. In one embodiment the mevalonate-kinase is a *Staphylococcus aureus* mevalonate-kinase encoded by a nucleic acid having the sequence set forth in SEQ ID No: 9. See FIG. 4A.

In one embodiment the phosphomevalonate kinase is the gene product of mvak2. In one embodiment the phosphomevalonate kinase is classified under EC 2.7.4.2. In one embodiment the phosphomevalonate kinase is a *Staphylococcus aureus* phosphomevalonate kinase (Genbank Accession No. BAB56754.1, SEQ ID No: 3). See FIG. 3A. In one embodiment the phosphomevalonate kinase is a *Staphylococcus aureus* phosphomevalonate kinase encoded by a nucleic acid having the sequence set forth in SEQ ID No: 10. See FIG. 4A.

In one embodiment the diphosphomevalonate decarboxylase is the gene product of Mdd. In one embodiment the diphosphomevalonate decarboxylase is classified under EC 4.1.1.33. In one embodiment the diphosphomevalonate decarboxylase is a *Streptococcus pneumoniae* diphosphomevalonate decarboxylase (Genbank Accession No. AAK99143.1, SEQ ID No: 4). See FIG. 3A. In one embodiment the diphosphomevalonate decarboxylase is a *Staphylococcus epidermidis* mevalonate diphosphate decarboxylase (Genbank Accession No. AAG02436.1, SEQ ID No. 5). See FIG. 3. In one embodiment the diphosphomevalonate decarboxylase is a *Streptococcus pneumoniae* diphosphomevalonate decarboxylase encoded by a nucleic acid having the sequence set forth in SEQ ID No: 11. See FIG. 4B.

In one embodiment the isopentenyl diphosphate isomerase is the gene product of idi. In one embodiment the isopentenyl diphosphate isomerase is classified under EC 5.3.3.2. In one embodiment the isopentenyl diphosphate isomerase is a *Burkholderia multivorans* isopentenyl diphosphate isomerase (Genbank Accession No. ABX19602.1, SEQ ID No: 6). See FIG. 3B. In one embodiment the isopentenyl diphosphate isomerase is a *Burkholderia multivorans* isopentenyl diphosphate isomerase encoded by a nucleic acid having the sequence set forth in SEQ ID No: 12. See FIG. 4C.

In one embodiment the isoprene synthase is the gene product of ispS. In one embodiment the isoprene synthase is classified under EC 4.2.3.27. In one embodiment the isoprene synthase is a *Mucuna pruhens* isoprene synthase (SEQ ID No: 7). See FIG. 3B. In one embodiment the isoprene synthase is classified under EC 4.2.3.27. In one embodiment the isoprene synthase is a *Mucuna pruriens* isoprene synthase encoded by a nucleic acid having the sequence set forth in SEQ ID No: 13. See FIG. 4D.

Within an engineered pathway, the enzymes can be from a single source, i.e., from one species, or can be from multiple sources, i.e., different species. Nucleic acids encoding the enzymes described herein have been identified from various organisms and are readily available in publicly available databases such as GenBank or EMBL.

Any of the enzymes described herein that can be used for 3-HMG production and/or isoprene production can have at least 70% sequence identity (homology) (e.g., at least 75%, 80%, 85%, 90%, 95%, 97%, 98%, 99%, or 100%) to the amino acid sequence of the corresponding wild-type enzyme.

For example, a hydroxymethylglutaryl Co-A reductase described herein can have at least 70% sequence identity (homology) (e.g., at least 75%, 80%, 85%, 90%, 95%, 97%, 98%, 99%, or 100%) to the amino acid sequence of a *Staphylococcus aureus* hydroxymethylglutaryl Co-A reductase (Genbank Accession No. BAB58707.1, SEQ ID No: 1). See FIG. 3A.

For example, a mevalonate-kinase described herein can have at least 70% sequence identity (homology) (e.g., at least 75%, 80%, 85%, 90%, 95%, 97%, 98%, 99%, or 100%) to the amino acid sequence of a *Staphylococcus aureus* mevalonate-kinase (Genbank Accession No. BAB56752.1, SEQ ID No: 2). See FIG. 3A.

For example, a phosphomevalonate kinase described herein can have at least 70% sequence identity (homology) (e.g., at least 75%, 80%, 85%, 90%, 95%, 97%, 98%, 99%, or 100%) to the amino acid sequence of a *Staphylococcus aureus* phosphomevalonate kinase (Genbank Accession No. BAB56754.1, SEQ ID No: 3). See FIG. 3A.

For example, a diphosphomevalonate decarboxylase described herein can have at least 70% sequence identity (homology) (e.g., at least 75%, 80%, 85%, 90%, 95%, 97%, 98%, 99%, or 100%) to the amino acid sequence of a *Streptococcus pneumoniae* diphosphomevalonate decarboxylase (Genbank Accession No. AAK99143.1, SEQ ID No: 4), or a *Staphylococcus epidermidis* mevalonate diphosphate decarboxylase (Genbank Accession No. AAG02436.1, SEQ ID No: 5). See FIG. 3A.

For example, an isopentenyl diphosphate isomerase described herein can have at least 70% sequence identity (homology) (e.g., at least 75%, 80%, 85%, 90%, 95%, 97%, 98%, 99%, or 100%) to the amino acid sequence of a *Burkholderia multivorans* isopentenyl diphosphate isomerase (Genbank Accession No. ABX19602.1, SEQ ID No: 8). See FIG. 3B.

For example, an isoprene synthase described herein can have at least 70% sequence identity (homology) (e.g., at least 75%, 80%, 85%, 90%, 95%, 97%, 98%, 99%, or 100%) to the amino acid sequence of a *Mucuna pruriens* isoprene synthase (SEQ ID No: 7). See FIG. 3B.

The percent identity (homology) between two amino acid sequences can be determined by any method known to those skilled in the art. In one embodiment, the percent identity (homology) can be determined by aligning the amino acid sequences using the BLAST 2 Sequences (B 12 seq) program from the stand-alone version of BLASTZ containing BLASTP version 2.0.14. This standalone version of BLASTZ can be obtained from the U.S. government's National Center for Biotechnology Information web site (www.ncbi.nlm.nih.gov). Instructions explaining how to use the B12 seq program can be found in the readme file accompanying BLASTZ. B12 seq performs a comparison between two amino acid sequences using the BLASTP algorithm. To compare two amino acid sequences, the options of B12 seq are set as follows: -i is set to a file containing the first amino acid sequence to be compared (e.g., C:\seql.txt); -j is set to a file containing the second amino acid sequence to be compared (e.g., C:\seq2.txt); -pis set to blastp; -o is set to any desired file name (e.g., C:\output.txt); and all other options are left at their default setting. For example, the following command can be used to generate an output file containing a comparison between two amino acid sequences: C:\B12 seq -i c:\seql.txt -j c:\seq2.txt -p blastp -o c:\output.txt. If the two compared sequences share homology (identity), then the designated output file will present those regions of homology as aligned sequences. If the two compared sequences do not share homology (identity), then the designated output file will not present aligned sequences. Similar procedures can be used for nucleic acid sequences except that blastn is used.

Once aligned, the number of matches is determined by counting the number of positions where an identical amino acid residue is presented in both sequences. The percent identity (homology) is determined by dividing the number of matches by the length of the full-length polypeptide amino acid sequence followed by multiplying the resulting value by 100. It is noted that the percent identity (homology) value is rounded to the nearest tenth. For example, 78.11, 78.12, 78.13, and 78.14 is rounded down to 78.1, while 78.15, 78.18, 78.17, 78.18, and 78.19 is rounded up to 78.2. It also is noted that the length value will always be an integer.

This application also provides (i) functional variants of the enzymes used in the methods of the application and (ii) functional variants of the functional fragments described above. Functional variants of the enzymes and functional fragments can contain additions, deletions, or substitutions relative to the corresponding wild-type sequences. Enzymes with substitutions will generally have not more than 50 (e.g., not more than one, two, three, four, five, six, seven, eight, nine, ten, 12, 15, 20, 25, 30, 35, 40, or 50) amino acid substitutions (e.g., conservative substitutions). This applies to any of the enzymes described herein and functional fragments, A conservative substitution is a substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a nonconservative substitution is a substitution of one amino acid for another with dissimilar characteristics.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

Functional fragments of any of the enzymes described herein can also be used in the methods described herein. The term "functional fragment" as used herein refers to a peptide fragment of a protein that has at least 25% (e.g., at least: 30%; 40%; 50%; 60%; 70%; 75%; 80%; 85%; 90%; 95%; 98%; 99%; 100%; or even greater than 100%) of the activity of the corresponding mature, full-length, wild-type protein. The functional fragment can generally, but not always, be comprised of a continuous region of the protein, wherein the region has functional activity.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. Additions (addition variants) include fusion proteins containing: (a) any of the enzymes described herein or a fragment thereof; and (b) internal or terminal (C or N) irrelevant or heterologous amino acid sequences. In the context of such fusion proteins, the term "heterologous amino acid sequences" refers to an amino acid sequence other than (a). A heterologous sequence can be, for example a sequence used for purification of the recombinant protein (e.g., FLAG, poly histidine (e.g., hexahistidine (SEQ ID No: 14)), hemaglutianin (HA), glutathione-S-transferase (GST), or maltosebinding protein (MBP)). Heterologous sequences also can be proteins useful as detectable markers, for example, luciferase, green fluorescent protein (GFP), or chloramphenicol acetyl transferase (CAT). In some embodiments, the fusion protein contains a signal sequence from another protein. In certain host cells (e.g., yeast host cells), expression and/or secretion of the target protein can be increased through use of a heterologous signal sequence. In some embodiments, the fusion protein can contain a carrier (e.g., KLH) useful, e.g., in eliciting an immune response for antibody generation) or ER or Golgi apparatus retention signals. Heterologous sequences can be of varying length and in some cases can be a longer sequences than the full-length target proteins to which the heterologous sequences are attached.

Hosts can naturally express none or some (e.g., one or more, two or more, three or more, four or more, five or more, or six or more) of the enzymes of the pathways described herein. Endogenous genes of the recombinant hosts also can be disrupted to prevent the formation of undesirable metabolites or prevent the loss of intermediates in the pathway through other enzymes acting on such intermediates. Recombinant hosts can be referred to as recombinant host cells, non-naturally occurring host cells, engineered cells, or engineered hosts. Thus, as described herein, recombinant hosts can include nucleic acids encoding one or more of a decarboxylase, a kinase, a dehydrogenase, a monooxygenase, an acyl [acyl carrier protein (acp)] dehydrogenase, a dehydratase, a thioesterase, or a decarboxyating thioesterase as described in more detail below.

In addition, the production of 3-HMG and/or isoprene can be performed in vitro using the isolated enzymes described herein, using a lysate (e.g., a cell lysate) from a host microorganism as a source of the enzymes, or using a plurality of lysates from different host microorganisms as the source of the enzymes.

Figure 2:
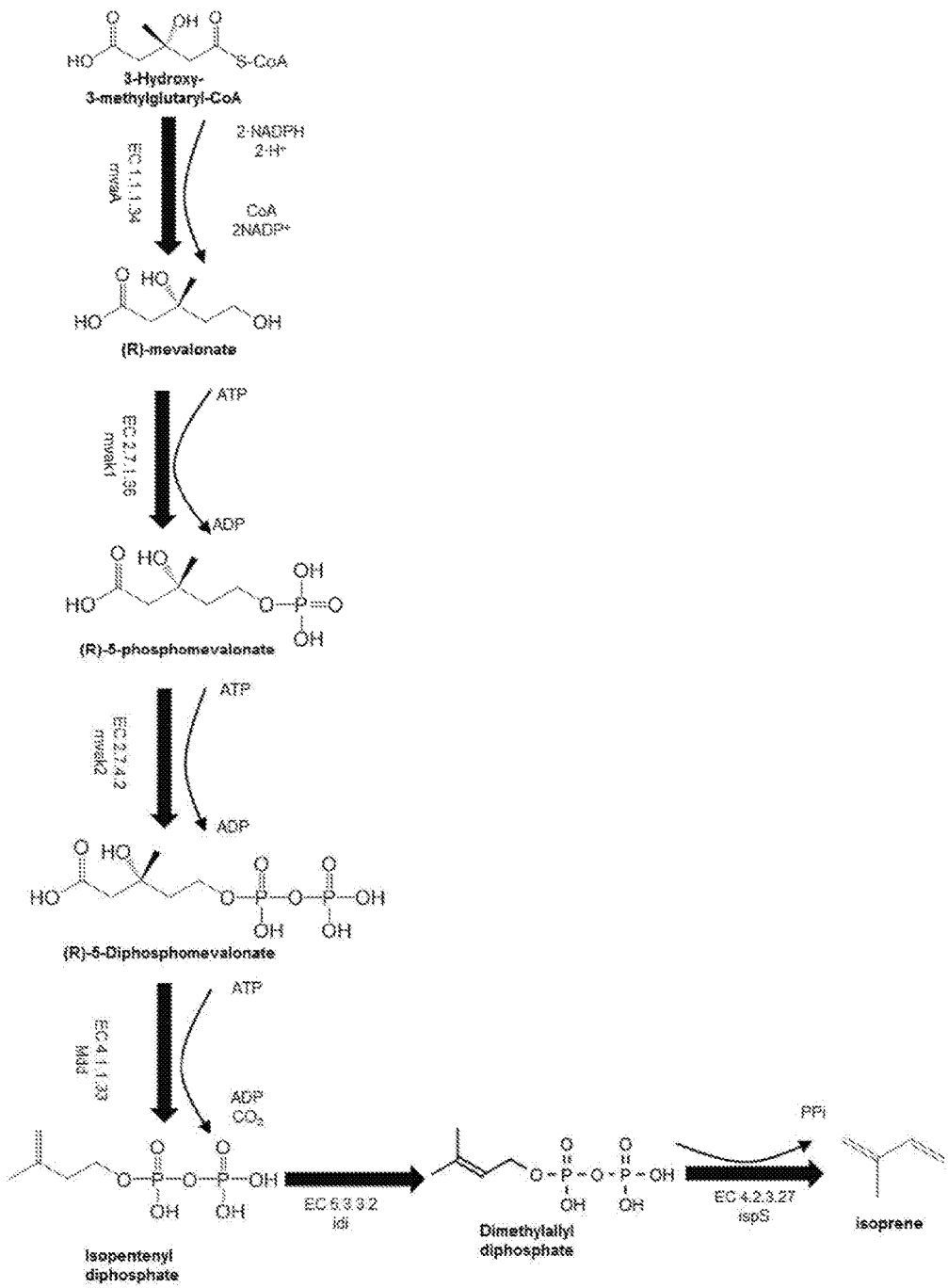
FIG. 2 is a schematic of an exemplary biochemical pathway leading to isoprene from 3-HMG via the mevalonate pathway.

In some embodiments, the enzymes of the pathways described in FIG. 1 and FIG. 2 are the result of enzyme engineering to improve activity or specificity using the enzyme structure and wild-type residue diversity to inform the rational enzyme design.

In some embodiments, the nucleic acids encoding the enzymes of the pathways described in FIG. 1 and FIG. 2 are introduced into a host microorganism that is either a prokaryote or eukaryote.

Cultivation Strategies

In some embodiments, the host microorganism is a prokaryote. For example, the prokaryote can be a bacterium from the genus *Escherichia* such as *Escherichia coli*; from the genus *Clostridia* such as *Clostridium ljungdahlii*, *Clostridium autoethanogenum* or *Clostridium kluyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens*, *Pseudomonas putida* or *Pseudomonas oleavorans*; from the genus *Delftia* such as *Delftia acidovorans*; from the genus *Bacillus* such as *Bacillus subtillis*; from the genus *Lactobacillus* such as *Lactobacillus delbrueckii*; or from the genus *Lactococcus* such as *Lactococcus lactis*. Such prokaryotes also can be a source of genes to construct recombinant host cells described herein that are capable of producing isoprene or precursors thereof.

In some embodiments, the host microorganism is a eukaryote. For example, the eukaryote can be a filamentous fungus, e.g., one from the genus *Aspergillus* such as *Aspergillus niger*. Alternatively, the eukaryote can be a yeast, e.g., one from the genus *Saccharomyces* such as *Saccharomyces cerevisiae*; from the genus *Pichia* such as *Pichia pastoris*; or from the genus *Yarrowia* such as *Yarrowia lipolytica*; from the genus *Issatchenkia* such as *Issatchenkia orientalis*; from the genus *Debaryomyces* such as *Debaryomyces hansenii*; from the genus *Arxula* such as *Arxula adeninivorans*; or from the genus *Kluyveromyces* such as *Kluyveromyces lactis*. Such eukaryotes also can be a source of genes to construct recombinant host cells described herein that are capable of producing isoprene or precursors thereof.

In some embodiments, 3-HMG is biosynthesized in a recombinant host using a fermentation strategy that can include anaerobic, micro-aerobic or aerobic cultivation of the recombinant host.

In some embodiments, 3-HMG is biosynthesized in a recombinant host using a fermentation strategy that uses an alternate final electron acceptor to oxygen such as nitrate.

In some embodiments, isoprene is biosynthesized in a recombinant host using a fermentation strategy that can include anaerobic, micro-aerobic or aerobic cultivation of the recombinant host.

In some embodiments, isoprene is biosynthesized in a recombinant host using a fermentation strategy that uses an alternate final electron acceptor to oxygen such as nitrate.

In some embodiments, a cell retention strategy using, for example, ceramic hollow fiber membranes can be employed to achieve and maintain a high cell density during either fed batch or continuous fermentation in the synthesis of 3-HMG and/or isoprene.

In some embodiments, the biological feedstock can be, can include, or can derive from, monosaccharides, disaccharides, lignocellulose, hemicellulose, cellulose, lignin, levulinic acid &, formic acid, triglycerides, glycerol, fatty acids, agricultural waste, condensed distillers' solubles, or municipal waste.

The efficient catabolism of crude glycerol stemming from the production of biodiesel has been demonstrated in several microorganisms such as *Escherichia coli, Cupriavidus necator, Pseudomonas oleavorans, Pseudomonas putida* and *Yarrowia lipolytica* (Lee et al., Appl. Biochem. Biotechnol., 2012, 166, 1801-1813; Yang et al., Biotechnology for Biofuels, 2012, 5:13; Meijnen et al., Appl. Microbial. Biotechnol., 2011, 90, 885-893).

The efficient catabolism of lignocellulosic-derived levulinic acid has been demonstrated in several organisms such as *Cupriavidus necator* and *Pseudomonas putida* in the synthesis of 3-hydroxyvalerate via the precursor propanoyl-CoA (Jaremko and Yu, Journal of Biotechnology, 2011, 155, 2011, 293-298; Martin and Prather, Journal of Biotechnology, 2009, 139, 61-67).

The efficient catabolism of lignin-derived aromatic compounds such benzoate analogues has been demonstrated in several microorganisms such as *Pseudomonas putida, Cupriavidus necator* (Bugg et al., Current Opinion in Biotechnology, 2011, 22, 394-400; Perez-Pantoja et al, FEMS Microbial. Rev., 2008, 32, 738-794).

The efficient utilization of agricultural waste, such as olive mill waste water has been demonstrated in several microorganisms, including *Yarrowia lipolytica* (Papanikolaou et al., Bioresour. Technol., 2008, 99(7), 2419-2428).

The efficient utilization of fermentable sugars such as monosaccharides and disaccharides derived from cellulosic, hemicellulosic, cane and beet molasses, cassava, corn and other agricultural sources has been demonstrated for several microorganism such as *Escherichia coli, Corynebacterium glutamicum* and *Lactobacillus delbrueckii* and *Lactococcus lactis* (see, e.g., Hermann et al, Journal of Biotechnology, 2003, 104, 155-172; Wee et al., Food Technol. Biotechnol., 2006, 44(2), 163-172; Ohashi et al., Journal of Bioscience and Bioengineering, 1999, 87(5), 647-654).

The efficient utilization of furfural, derived from a variety of agricultural lignocellulosic sources, has been demonstrated for *Cupriavidus necator* (Li et al., Biodegradation, 2011, 22, 1215-1225).

In some embodiments, the non-biological feedstock can be or can derive from natural gas, syngas, $CO_2/H_2$, methanol, ethanol, benzoic acid, non-volatile residue (NVR) or a caustic wash waste stream from cyclohexane oxidation processes, or terephthalic acid/isophthalic acid mixture waste streams.

The efficient catabolism of methanol has been demonstrated for the methylotropic yeast *Pichia pastoris*.

The efficient catabolism of ethanol has been demonstrated for *Clostridium kluyveri* (Seedorf et al., Proc. Natl. Acad. Sci. USA, 2008, 105(6) 2128-2133). The efficient catabolism of $CO_2$ and $H_2$, which may be derived from natural gas and other chemical and petrochemical sources, has been demonstrated for *Cupriavidus necator* (Prybylski et al., Energy, Sustainability and Society, 2012, 2:11).

The efficient catabolism of syngas has been demonstrated for numerous microorganisms, such as *Clostridium ljungdahlii* and *Clostridium autoethanogenum* (Kopke et al., Applied and Environmental Microbiology, 2011, 77(15), 5487-5475).

The efficient catabolism of the non-volatile residue waste stream from cyclohexane processes has been demonstrated for numerous microorganisms, such as *Delftia acidovorans* and *Cupriavidus necator* (Ramsay et al., Applied and Environmental Microbiology, 1988, 52(1), 152-156).

In some embodiments, substantially pure cultures of recombinant host microorganisms are provided. As used herein, a "substantially pure culture" of a recombinant host microorganism is a culture of that microorganism in which less than about 40% (i.e., less than about 35%; 30%; 25%; 20%; 15%; 10%; 5%; 2%; 1%; 0.5%; 0.25%; 0.1%; 0.01%; 0.001%; 0.0001%; or even less) of the total number of viable cells in the culture are viable cells other than the recombinant microorganism, e.g., bacterial, fungal (including yeast), mycoplasmal, or protozoan cells. The term "about" in this context means that the relevant percentage can be 15% of the specified percentage above or below the specified percentage. Thus, for example, about 20% can be 17% to 23%. Such a culture of recombinant microorganisms includes the cells and a growth, storage, or transport medium. Media can be liquid, semi-solid (e.g., gelatinous media), or frozen. The culture includes the cells growing in the liquid or inion the semi-solid medium or being stored or transported in a storage or transport medium, including a frozen storage or transport medium. The cultures are in a culture vessel or storage vessel or substrate (e.g., a culture dish, flask, or tube or a storage vial or tube).

Metabolic Engineering

The present application provides methods involving less than or more than all the steps described for all the above pathways. Such methods can involve, for example, one, two, three, four, five, six, seven, eight, nine, ten, or more of such steps. Where less than all the steps are included in such a method, the first step can be any one of the steps listed. Furthermore, recombinant hosts described herein can include any combination of the above enzymes such that one or more of the steps, e.g., one, two, three, four, five, six, seven, eight, nine, ten, or more of such steps, can be performed within a recombinant host.

In addition, this application recognizes that where enzymes have been described as accepting CoA-activated substrates, analogous enzyme activities associated with [acp]-bound substrates exist that are not necessarily in the same enzyme class.

Also, this application recognizes that where enzymes have been described accepting (R)-enantiomers of substrate, analogous enzyme activities associated with (S)-enantiomer substrates exist that are not necessarily in the same enzyme class.

This application also recognizes that where an enzyme is shown to accept a particular co-factor, such as NADPH, or co-substrate, such as but not limited to 3-methylglutaconyl-coA, many enzymes are promiscuous in terms of accepting a number of different co-factors or co-substrates in catalyzing a particular enzyme activity. Also, this application recognizes that where enzymes have high specificity for e.g., a particular co-factor such as NADH, an enzyme with similar or identical activity that has high specificity for the co-factor NADPH may be in a different enzyme class.

In some embodiments, the enzymes in the pathways outlined herein can be the result of enzyme engineering via non-direct or rational enzyme design approaches with aims of improving activity, improving specificity, reducing feedback inhibition, reducing repression, improving enzyme solubility, changing stereo-specificity, or changing co-factor specificity.

In some embodiments, the enzymes in the pathways outlined herein can be gene dosed, i.e., overexpressed, into the resulting genetically modified organism via episomal or chromosomal integration approaches.

In some embodiments, genome-scale system biology techniques such as Flux Balance Analysis can be utilized to devise genome scale attenuation or knockout strategies for directing carbon flux to isoprene.

In some embodiments, fluxomic, metabolomic and transcriptomal data can be utilized to inform or support genome-scale system biology techniques, thereby devising genome scale attenuation or knockout strategies in directing carbon flux to isoprene.

In some embodiments, one or more enzymes from the pathways described herein, for example, at least one enzyme classified under EC 1.2.1-, EC 1.2.7.7, EC 4.1.1.74, EC 4.1.1.43, EC 1.2.1.39, EC 1.2.15, EC 6.2.1.-, EC 1.3.8.4, EC 8.4.1.4, EC 4.2.1.18, EC 1.1.1.34, EC 2.7.1.36, EC 2.7.4.2, EC 4.1.1.33, EC 5.3.3.2, or EC 4.2.3.27, are introduced or gene dosed into a host microorganism that utilizes the non-mevalonate or 2-C-methyl-D-erythritol 4-phosphate pathway for isoprenoid synthesis. In some embodiments, at least one enzyme having the amino acid sequence listed in SEQ ID No: 1, SEQ ID No: 2, SEQ ID No: 3, SEQ ID No: 4, SEQ ID No: 59, SEQ ID No: 8, or SEQ ID No: 7 is introduced or gene dosed into a host microorganism that utilizes the non-mevalonate or 2-C-methyl-D-erythritol 4-phosphate pathway for isoprenoid synthesis.

In some embodiments, where pathways require excess NADPH co-factor in the synthesis of isoprene, a puridine nucleotide transhydrogenase gene such as UdhA can be overexpressed in the host organism (Brigham et al., Advanced Biofuels and Bioproducts, 2012, Chapter 39, 1065-1090).

In some embodiments, where pathways require excess NADPH co-factor in the synthesis of isoprene, a glyceraldehyde-3P-dehydrogenase gene such as GapN can be overexpressed in the host organism (Brigham et al., 2012, supra).

In some embodiments, where pathways require excess NADPH co-factor in the synthesis of isoprene, a malic enzyme gene such as macA or maeB can be overexpressed in the host organism (Brigham et al., 2012, supra).

In some embodiments, where pathways require excess NADPH co-factor in the synthesis of isoprene, a glucose-6-phosphate dehydrogenase gene such as zwf can be overexpressed in the host organism (Lim et al., Journal of Bioscience and Bioengineering, 2002, 93(8), 543-549).

In some embodiments, where pathways require excess NADPH co-factor in the synthesis of isoprene, a fructose 1,6 diphosphatase gene such as fbp can be overexpressed in the host (Becker et al., Journal of Biotechnology, 2007, 132, 99-109).

In some embodiments, the efflux of isoprene across the cell membrane to the extracellular media can be enhanced or amplified by genetically engineering structural modifications to the cell membrane or increasing any associated transporter activity for isoprene.

Producing Isoprene Using a Recombinant Host

3-HMG and/or isoprene can be produced by providing a host microorganism and culturing the provided microorganism with a culture medium containing a suitable carbon source as described above. In general, the culture media and/or culture conditions can be such that the microorganisms grow to an adequate density and produce isoprene efficiently. For large-scale production processes, any method can be used such as those described elsewhere (Manual of Industrial Microbiology and Biotechnology, 2nd Edition, Editors: A. L. Demain and J. E. Davies, ASM Press; and Principles of Fermentation Technology, P. F. Stanbury and A. Whitaker, Pergamon). In one example, a large tank (e.g., a 100 gallon, 200 gallon, 500 gallon, or more tank) containing an appropriate culture medium is inoculated with a particular microorganism. After inoculation, the microorganism is incubated to allow biomass to be produced. Once a desired biomass is reached, the broth containing the microorganisms can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank.

Once transferred, the microorganisms can be incubated to allow for the production of 3-HMG and/or isoprene. In one example, a substrate comprising CO is provided to a bioreactor comprising one or more microorganisms and anaerobically fermenting the substrate to produce isoprene according to methods described in US 2012/0045807. In one example, the microorganisms can be used for the production of isoprene by microbial fermentation of a substrate comprising CO according to methods described in US 2013/0323820.

Once produced, any method can be used to isolate isoprene. For example, isoprene can be recovered from the fermenter off-gas stream as a volatile product as the boiling point of isoprene is 34.1° C. At a typical fermentation temperature of approximately 30° C., isoprene has a high vapor pressure and can be stripped by the gas flow rate through the broth for recovery from the off-gas. Isoprene can be selectively adsorbed onto, for example, an adsorbent and separated from the other off-gas components. Membrane separation technology may also be employed to separate isoprene from the other off-gas compounds. Isoprene may desorbed from the adsorbent using, for example, nitrogen and condensed at low temperature and high pressure.

Additional Exemplary Embodiments

In one embodiment, are methods for synthesizing 3-hydroxy-3-methylglutaryl-CoA comprising: enzymatically converting 4-methyl-2-oxopentanoate to 3-methylbutanoyl-CoA, for example by using a polypeptide having the activity of an EC 1.2.7.7 or EC 1.2.1.-enzyme; enzymatically converting 3-methylbutanoyl-CoA to 3-methylbut-2-enoyl-CoA, for example by using a polypeptide having the activity of an EC 1.3.8.4 enzyme; enzymatically converting 3-methylbut-2-enoyl-CoA to 3-methyl-glutaconyl-CoA, for example by using a polypeptide having the activity of an EC 6.4.1.4 enzyme; and enzymatically converting 3-methyl-glutaconyl-CoA to 3-hydroxy-3-methylglutaryl-CoA, for example by using a polypeptide having the activity of an EC 4.2.1.18 enzyme.

In one embodiment are methods for synthesizing 3-hydroxy-3-methylglutaryl-CoA comprising: enzymatically converting 4-methyl-2-oxopentanoate to 3-methylbutanal, for example by using a polypeptide having the activity of an EC 4.1.1.74 or EC 4.1.1.43 enzyme; enzymatically converting 3-methylbutanal to 3-methylbutanoate, for example by using a polypeptide having the activity of an EC 1.2.1.39 or EC 1.2.1.5 enzyme; enzymatically converting 3-methylbutanoate to 3-methylbutanoyl-CoA, for example by using a polypeptide having the activity of an EC 6.2.1.2 enzyme; enzymatically converting 3-methylbutanoyl-CoA to 3-methylbut-2-enoyl-CoA, for example by using a polypeptide having the activity of an EC 1.3.8.4 enzyme; enzymatically converting 3-methylbut-2-enoyl-CoA to 3-methyl-glutaconyl-CoA, for example by using a polypeptide having the activity of an EC 6.4.1.4 enzyme; and enzymatically converting 3-methyl-glutaconyl-CoA to 3-hydroxy-3-methyl-glutaryl-CoA, for example by using a polypeptide having the activity of an EC 4.2.1.18 enzyme.

In one embodiment are provided methods for synthesizing 3-hydroxy-3-methylglutaryl-CoA comprising: enzymatically converting 4-methyl-2-oxopentanoate to 3-methylbut-2-enoyl-CoA by: (a) enzymatically converting 4-methyl-2-oxopentanoate to 3-methylbutanal, enzymatically converting 3-methylbutanal to 3-methylbutanoate, and enzymatically converting 3-methylbutanoate to 3-methylbutanoyl-CoA; (b) enzymatically converting 4-methyl-2-oxopentanoate to 3-methylbutanoyl-CoA; or (c) both (a) and (b); enzymatically converting 3-methylbutanoyl-CoA to 3-methylbut-2-enoyl-CoA; enzymatically converting 3-methylbut-2-enoyl-CoA to 3-methyl-glutaconyl-CoA; and enzymatically converting 3-methyl-glutaconyl-CoA to 3-hydroxy-3-methylglutaryl-CoA.

In one embodiment are provided methods for synthesizing 3-hydroxy-3-methylglutaryl-CoA comprising: enzymatically converting 4-methyl-2-oxopentanoate to 3-methylbut-2-enoyl-CoA by: both (a) enzymatically converting 4-methyl-2-oxopentanoate to 3-methylbutanal, enzymatically converting 3-methylbutanal to 3-methylbutanoate, and enzymatically converting 3-methylbutanoate to 3-methylbutanoyl-CoA; and (b) enzymatically converting 4-methyl-2-oxopentanoate to 3-methylbutanoyl-CoA; enzymatically converting 3-methylbutanoyl-CoA to 3-methylbut-2-enoyl-CoA; enzymatically converting 3-methylbut-2-enoyl-CoA to 3-methyl-glutaconyl-CoA; and enzymatically converting 3-methyl-glutaconyl-CoA to 3-hydroxy-3-methylglutaryl-CoA.

In one embodiment are provided methods for synthesizing isoprene via a mevalonate pathway comprising: synthesizing 3-hydroxy-3-methylglutaryl-CoA according to a method described herein: enzymatically converting 3-hydroxy-3-methylglutaryl-CoA to (R)-mevalonate; enzymatically converting (R)-mevalonate to (R)-5-phosphomevalonate; enzymatically converting (R)-5-phosphomevalonate to (R)-5-diphosphomevalonate; enzymatically converting (R)-5-diphosphomevalonate to isopentenyl diphosphate; enzymatically converting isopentenyl diphosphate to dimethylallyl diphosphate; and enzymatically converting dimethylallyl diphosphate to isoprene.

In one embodiment are provided methods for synthesizing isoprene via a mevalonate pathway comprising: synthesizing S-hydroxy-S-methylglutaryl-CoA according to a method described herein; and one or more steps selected from the group consisting of: enzymatically converting 3-hydroxy-3-methylglutaryl-CoA to (R)-mevalonate using a polypeptide having the activity of an EC 1.1.1.34 enzyme; enzymatically converting (R)-mevalonate to (R)-5-phosphomevalonate using a polypeptide having the activity of an EC 2.7.1.38 enzyme; enzymatically converting (R)-5-phosphomevalonate to (R)-5-diphosphomevalonate using a polypeptide having the activity of an EC 2.7.4.2 enzyme; enzymatically converting (R)-5-diphosphomevalonate to isopentenyl diphosphate using a polypeptide having the activity of an EC 4.1.1.33 enzyme; enzymatically converting isopentenyl diphosphate to dimethylallyl diphosphate using a polypeptide having the activity of an EC 5.3.3.2 enzyme; and enzymatically converting dimethylallyl diphosphate to isoprene using a polypeptide having the activity of an EC 4.2.3.27 enzyme.

In one embodiment is provided a non-naturally occurring host capable of producing 3-hydroxy-3-methylglutaryl-CoA, said host comprising: at least one exogenous nucleic acid encoding a polypeptide having the activity of an EC 1.2.7.7 or EC 1.2.1.-enzyme; at least one exogenous nucleic acid encoding a polypeptide having the activity of an EC 1.3.8.4 enzyme; at least one exogenous nucleic acid encoding a polypeptide having the activity of an EC 6.4.1.4 enzyme; and at least one exogenous nucleic acid encoding a polypeptide having the activity of an EC 4.2.1.18 enzyme.

In one embodiment is provided a non-naturally occurring host capable of producing 3-hydroxy-3-methylglutaryl-CoA, said host comprising: at least one exogenous nucleic acid encoding a polypeptide having the activity of an EC 4.1.1.74 or EC 4.1.1.43 enzyme; at least one exogenous nucleic acid encoding a polypeptide having the activity of an EC 1.2.1.39 or EC 1.2.1.5 enzyme; at least one exogenous nucleic acid encoding a polypeptide having the activity of an EC 8.2.1.2. enzyme; at least one exogenous nucleic acid encoding a polypeptide having the activity of an EC 1.3.8.4 enzyme; at least one exogenous nucleic acid encoding a polypeptide having the activity of an EC 8.4.1.4 enzyme; and at least one exogenous nucleic acid encoding a polypeptide having the activity of an EC 4.2.1.18 enzyme.

In one embodiment is provided a non-naturally occurring host capable of producing 3-hydroxy-3-methylglutaryl-CoA, said host comprising: at least one exogenous nucleic acid encoding a polypeptide having the activity of an EC 1.2.7.7 or EC 1.2.1.-enzyme; at least one exogenous nucleic acid encoding a polypeptide having the activity of an EC 4.1.1.74 or EC 4.1.1.43 enzyme; at least one exogenous nucleic acid encoding a polypeptide having the activity of an EC 1.2.1.39 or EC 1.2.1.5 enzyme; at least one exogenous nucleic acid encoding a polypeptide having the activity of an EC 8.2.1.2. enzyme; at least one exogenous nucleic acid encoding a polypeptide having the activity of an EC 1.3.8.4 enzyme; at least one exogenous nucleic acid encoding a polypeptide having the activity of an EC 6.4.1.4 enzyme; and at least one exogenous nucleic acid encoding a polypeptide having the activity of an EC 4.2.1.18 enzyme.

In one embodiment is provided a non-naturally occurring host as described above wherein said host is capable of producing isoprene and comprises: at least one exogenous nucleic acid encoding a polypeptide having the activity of an EC 1.1.1.34 enzyme; at least one exogenous nucleic acid encoding a polypeptide having the activity of an EC 2.7.1.38 enzyme; at least one exogenous nucleic acid encoding a polypeptide having the activity of an EC 2.7.4.2 enzyme; at least one exogenous nucleic acid encoding a polypeptide having the activity of an EC 4.1.1.33 enzyme; at least one exogenous nucleic acid encoding a polypeptide having the activity of an EC 5.3.3.2 enzyme; and at least one exogenous nucleic acid encoding a polypeptide having the activity of an EC 4.2.3.27 enzyme.

In one embodiment is provided a non-naturally occurring host capable of producing 3-hydroxy-3-methylglutaryl-CoA, said host comprising at least one of: at least one exogenous nucleic acid encoding a polypeptide having the activity of an EC 1.2.7.7 or EC 1.2.1.-enzyme; at least one exogenous nucleic acid encoding a polypeptide having the activity of an EC 4.1.1.74 or EC 4.1.1.43 enzyme; at least one exogenous nucleic acid encoding a polypeptide having the activity of an EC 1.2.1.39 or EC 1.2.1.5 enzyme; at least one exogenous nucleic acid encoding a polypeptide having the activity of an EC 6.2.1.2. enzyme; at least one exogenous nucleic acid encoding a polypeptide having the activity of an EC 1.3.8.4 enzyme; at least one exogenous nucleic acid encoding a polypeptide having the activity of an EC 6.4.1.4 enzyme; and at least one exogenous nucleic acid encoding a polypeptide having the activity of an EC 4.2.1.18 enzyme; and said host further comprising at least one of: at least one endogenous enzyme capable of enzymatically converting 4-methyl-2-oxopentanoate to 3-methylbutanoyl-CoA; at least one endogenous enzyme capable of enzymatically converting 4-methyl-2-oxopentanoate to 3-methylbutanal; at least one endogenous enzyme capable of enzymatically converting 3-methylbutanal to 3-methylbutanoate; at least one endogenous enzyme capable of enzymatically converting 3-methylbutanoate to 3-methylbutanoyl-CoA; at least one endogenous enzyme capable of enzymatically converting 3-methylbutanoyl-CoA to 3-methylbut-2-enoyl-CoA; at least one endogenous enzyme capable of 3-methylbut-2-enoyl-CoA to 3-methyl-glutaconyl-CoA; and at least one endogenous enzyme capable of 3-methyl-glutaconyl-CoA to 3-hydroxy-3-methylglutaryl-CoA.

In one embodiment is provided a non-naturally occurring host as described above wherein at least one of the exogenous nucleic acids is contained within a plasmid.

In one embodiment is provided a non-naturally occurring host as described above wherein at least one of the exogenous nucleic acids is integrated into a chromosome of the host.

In one embodiment is provide a method as described above wherein said method is performed in a recombinant host.

In one embodiment is provide a method as described above wherein at least one of the enzymatic conversions is performed in a recombinant host.

In one embodiment the host is a prokaryotic host, for example from the genus *Escherichia, Clostridia, Corynebacteria, Cupriavidus, Pseudomonas, Bacillus*, or *Rhodococcus*. In one embodiment the host is *Cupriavidus necator*.

In one embodiment the host is a eukaryotic host, for example from the genus *Aspergillus, Saccharomyces, Pichia, Yarrowia, Issatchenkia, Debaryomyces, Arxula*, or *Kluyveromyces*.

In one embodiment the host is capable of endogenously producing 3-hydroxy-3-methylglutaryl-CoA.

In one embodiment the host is capable of endogenously producing isoprene via a non-mevalonate pathway.

In one embodiment of the methods and hosts described herein, at least one of the enzymatic conversions comprises gas fermentation within the host, for example fermentation of gas comprising at least one of natural gas, syngas, $CO_2/H_2$, methanol, ethanol, non-volatile residue, caustic wash from cyclohexane oxidation processes, or waste stream from a chemical or petrochemical industry.

In one embodiment is provided a method for synthesizing 3-hydroxy-3-methylglutaryl-CoA comprising culturing a host described herein in a gas medium.

In one embodiment is provided a method for synthesizing isoprene via the mevalonate pathway comprising culturing a host described herein in a gas medium. In one embodiment the method further comprises recovering the produced isoprene. In one embodiment, the host performs the enzymatic synthesis by gas fermentation. In one embodiment, the gas comprises at least one of natural gas, syngas, $CO_2/H_2$, methanol, ethanol, non-volatile residue, caustic wash from cyclohexane oxidation processes, or waste stream from a chemical or petrochemical industry.

In one embodiment is provided a composition comprising 3-hydroxy-3-methylglutaryl-CoA synthesized by a method described herein.

In one embodiment is provided a composition comprising isoprene synthesized by a method described herein.

In one embodiment is provided a method for producing bioderived 3-hydroxy-3-methylglutaryl-CoA, comprising culturing or growing a host described herein under conditions and for a sufficient period of time to produce bio-derived 3-hydroxy-3-methylglutaryl-CoA.

In one embodiment is provided a method for producing bioderived isoprene, comprising culturing or growing a host described herein under conditions and for a sufficient period of time to produce bioderived isoprene.

In one embodiment is provided bioderived isoprene produced in a host described herein, wherein said bioderived isoprene has a carbon-12, carbon-13, and carbon-14 isotope ratio that reflects an atmospheric carbon dioxide uptake source.

In one embodiment is provided a bio-derived, bio-based, or fermentation-derived product comprising: (a) a composition comprising at least one bio-derived, bio-based, or fermentation-derived compound prepared (i) using a host described herein, or (ii) according to a method described herein, or any combination thereof; (b) a bio-derived, bio-based, or fermentation-derived polymer comprising the bio-derived, bio-based, or fermentation-derived composition or compound of (a), or any combination thereof; (c) a bio-derived, bio-based, or fermentation-derived cis-polyisoprene rubber, trans-polyisoprene rubber, or liquid polyisoprene rubber, comprising the bio-derived, bio-based, or fermentation-derived compound or bio-derived, bio-based, or fermentation-derived composition of (a), or any combination thereof or the bio-derived, bio-based, or fermentation-derived polymer of (b), or any combination thereof; (d) a molded substance obtained by molding the bio-derived, bio-based, or fermentation-derived polymer of (b), or the bio-derived, bio-based, or fermentation-derived resin of (c), or any combination thereof; (e) a bio-derived, bio-based, or fermentation-derived formulation comprising the bio-derived, bio-based, or fermentation-derived composition or compound of (a), bio-derived, bio-based, or fermentation-derived polymer of (b), bio-derived, bio-based, or fermentation-derived resin of (c), or bio-derived, bio-based, or fermentation-derived molded substance of (d), or any combination thereof; or (f) a bio-derived, bio-based, or fermentation-derived semi-solid or a non-semi-solid stream, comprising the bio-derived, bio-based, or fermentation-derived composition or compound of (a), bio-derived, bio-based, or fermentation-derived polymer of (b), bio-derived, bio-based, or fermentation-derived resin of (c), bio-derived, bio-based, or fermentation-derived formulation of (e), or bio-derived, bio-based, or fermentation-derived molded substance of (d), or any combination thereof.

Others Embodiments

It is to be understood that while the invention has been described in conjunction with the detailed description thereof, the foregoing description is intended to illustrate and not limit the scope of the invention. Other aspects, advantages, and modifications are within the scope of the following claims.

What is claimed is:

1. A method for synthesizing 3-hydroxy-3-methylglutaryl-CoA comprising:
   enzymatically converting 4-methyl-2-oxopentanoate to 3-methylbut-2-enoyl-CoA by:
   (a) enzymatically converting 4-methyl-2-oxopentanoate to 3-methylbutanal; enzymatically converting 3-methylbutanal to 3-methylbutanoate; and enzymatically converting 3-methylbutanoate to 3-methylbutanoyl-CoA;
   (b) enzymatically converting 4-methyl-2-oxopentanoate to 3-methylbutanoyl-CoA; or
   (c) both (a) and (b);
   enzymatically converting 3-methylbutanoyl-CoA to 3-methylbut-2-enoyl-CoA;
   enzymatically converting 3-methylbut-2-enoyl-CoA to 3-methyl-glutaconyl CoA; and
   enzymatically converting 3-methyl-glutaconyl-CoA to 3-hydroxy-3-methylglutaryl-CoA.

2. The method of claim 1, further comprising synthesizing isoprene via a mevalonate pathway comprising one or more steps selected from the group consisting of:
   enzymatically converting 3-hydroxy-3-methylglutaryl-CoA to (R)-mevalonate;
   enzymatically converting (R)-mevalonate to (R)-5-phosphomevalonate;
   enzymatically converting (R)-5-phosphomevalonate to (R)-5-diphosphomevalonate;
   enzymatically converting (R)-5-diphosphomevalonate to isopentenyl diphosphate;
   enzymatically converting isopentenyl diphosphate to dimethylallyl diphosphate; and
   enzymatically converting dimethylallyl diphosphate to isoprene.

3. The method of claim 1, wherein said method is performed in a recombinant host.

4. The method of claim 1, wherein at least one of the enzymatic conversions is performed in a recombinant host.

5. The method of claim 4, wherein the host is a prokaryotic host from the genus *Escherichia*, *Clostridia*, *Corynebacteria*, *Cupriavidus*, *Pseudomonas*, *Bacillus*, or *Rhodococcus*.

6. The method of claim 5, wherein the host is *Cupriavidus necator*.

7. The method of claim 4, wherein the host is a eukaryotic host from the genus *Aspergillus*, *Saccharomvces*, *Pichia*, *Yarrowia*, *Issatchenkia*, *Debaryomvces*, *Arxula*, or *Kluvveromvces*.

8. The method of claim 4, wherein the host is capable of endogenously producing 3-hydroxy-3-methylglutaryl-CoA.

9. The method of claim 4, wherein at least one of the enzymatic conversions comprises gas fermentation within the host.

10. The method of claim 9, wherein the gas comprises at least one of natural gas, syngas, $CO_2/H_2$, methanol, ethanol, non-volatile residue, caustic wash from cyclohexane oxidation processes, or waste stream from a chemical or petrochemical industry.

11. The method of claim 10, wherein the gas is $CO_2/H_2$.

12. A method for synthesizing 3-hydroxy-3-methylglutaryl-CoA comprising:
   enzymatically converting 4-methyl-2-oxopentanoate to 3-methylbut-2-enoyl-CoA by:
   (a) enzymatically converting 4-methyl-2-oxopentanoate to 3-methylbutanal using a polypeptide having the activity of an EC 4.1.1.74 or EC 4.1.1.43 enzyme;
   enzymatically converting 3-methylbutanal to 3-methylbutanoate using a polypeptide having the activity of an EC 1.2.1.39 or EC 1.2.1.5 enzyme; and
   enzymatically converting 3-methylbutanoate to 3-methylbutanoyl-CoA using a polypeptide having the activity of an EC 6.2.1.2 enzyme;
   (b) enzymatically converting 4-methyl-2-oxopentanoate to 3-methylbutanoyl-CoA using a polypeptide having the activity of an EC 1.2.7.7 or EC 1.2.1 enzyme; or
   (c) both (a) and (b);

enzymatically converting 3-methylbutanoyl-CoA to 3-methylbut-2-enoyl-CoA using a polypeptide having the activity of an EC 1.3.8.4 enzyme;

enzymatically converting 3-methylbut-2-enoyl-CoA to 3-methyl-glutaconyl CoA using a polypeptide having the activity of an EC 6.4.1.4 enzyme; and enzymatically converting 3-methyl-glutaconyl-CoA to 3-hydroxy-3-methylglutaryl-CoA using a polypeptide having enzyme activity classified under EC 4.2.1.18.

13. The method of claim 12, wherein the step of enzymatically converting 4-methyl-2-oxopentanoate to 3-methylbutanal comprises using a polypeptide having enzyme activity classified under EC 4.1.1.74.

14. The method of claim 13, wherein the polypeptide having enzyme activity classified under EC 4.1.1.74 is the gene product of ipdC.

15. The method of claim 12, wherein the step of enzymatically converting 3-methylbutanal to 3-methylbutanoate comprises using a polypeptide having enzyme activity classified under EC 1.2.1.39.

16. The method of claim 15, wherein the polypeptide having enzyme activity classified under EC 1.2.1.39 is the gene product of padA.

17. The method of claim 12, wherein the polypeptide having enzyme activity classified under EC 1.3.8.4 is the gene product of liuA.

* * * * *

UNITED STATES PATENT AND TRADEMARK OFFICE
CERTIFICATE OF CORRECTION

PATENT NO. : 10,167,487 B2  
APPLICATION NO. : 15/238234  
DATED : January 1, 2019  
INVENTOR(S) : Alex Van Eck Conradie Page 1 of 1

It is certified that error appears in the above-identified patent and that said Letters Patent is hereby corrected as shown below:

In the Claims

Claim 7, Column 44, Line 37, "*Saccharomvces*" should read --*Saccharomyces*--.

Signed and Sealed this  
Twenty-sixth Day of March, 2019

Andrei Iancu  
*Director of the United States Patent and Trademark Office*